(12) United States Patent
Fu et al.

(10) Patent No.: US 7,894,649 B2
(45) Date of Patent: Feb. 22, 2011

(54) TARGET TRACKING USING DIRECT TARGET REGISTRATION

(75) Inventors: Dongshan Fu, Santa Clara, CA (US); Robert D. Khan, Santa Cruz, CA (US); Hongwu Wang, Milpitas, CA (US); Bai Wang, Palo Alto, CA (US); Zhiping Mu, Foster City, CA (US); Matthew A. Core, San Jose, CA (US); Gopinath Kuduvalli, San Jose, CA (US); Calvin R. Maurer, Jr., Mountain View, CA (US)

(73) Assignee: Accuray Incorporated, Sunnyvale, CA (US)

( * ) Notice: Subject to any disclaimer, the term of this patent is extended or adjusted under 35 U.S.C. 154(b) by 1147 days.

(21) Appl. No.: 11/592,789

(22) Filed: Nov. 2, 2006

(65) Prior Publication Data
US 2008/0130825 A1    Jun. 5, 2008

(51) Int. Cl.
*G06K 9/00* (2006.01)
*A61B 6/10* (2006.01)
*A61N 5/10* (2006.01)
(52) U.S. Cl. .............................. 382/128; 378/8; 378/65
(58) Field of Classification Search ................. 382/103, 382/107, 128–134, 151, 294; 348/154, 155, 348/169–172; 600/407, 411, 429, 528, 585, 600/627, 9, 23, 26, 410, 427; 378/4, 8, 65, 378/69, 21–27, 101, 901; 128/920, 922
See application file for complete search history.

(56) References Cited

U.S. PATENT DOCUMENTS

| | | | | |
|---|---|---|---|---|
| 6,307,914 | B1 * | 10/2001 | Kunieda et al. | 378/65 |
| 6,501,981 | B1 * | 12/2002 | Schweikard et al. | 600/427 |
| 6,621,889 | B1 * | 9/2003 | Mostafavi | 378/65 |
| 6,889,695 | B2 * | 5/2005 | Pankratov et al. | 128/898 |
| 7,194,120 | B2 * | 3/2007 | Wicker et al. | 382/128 |
| 7,438,685 | B2 * | 10/2008 | Burdette et al. | 600/439 |
| 7,609,810 | B2 * | 10/2009 | Yi et al. | 378/65 |
| 2004/0042583 | A1 | 3/2004 | Wackerle et al. | |
| 2005/0075563 | A1 | 4/2005 | Sukovic et al. | |

OTHER PUBLICATIONS

PCT, International Search Report, International Application No. PCT/US 07/21884, filed Oct. 11, 2007, Mailed Apr. 2, 2008, 4 Pages.
PCT, Written Opinion of the International Searching Authority, International Application No. PCT/US 07/21884, filed Oct. 11, 2007, Mailed Apr. 2, 2008, 8 Pages.
Coste-Manière, È., "Robotic whole body stereotactic radiosurgery: clinical advantages of the CyberKnife® integrated system", The International Journal of Medical Robotics +Computer Assisted Surgery, 2005, www.roboticpublications.com, pp. 28-39.

(Continued)

*Primary Examiner*—Abolfazl Tabatabai
(74) *Attorney, Agent, or Firm*—Blakely, Sokoloff, Taylor & Zafman LLP

(57) ABSTRACT

Systems, methods and apparatus for directly tracking radiation targets during image-guided radiation treatment using 2D contouring and adaptive windowing.

42 Claims, 21 Drawing Sheets

OTHER PUBLICATIONS

PCT International Preliminary Report on Patentability, PCT/US2007/021884 filed Oct. 11, 2007, mailed May 14, 2009.

"A Comparison of 2D-3D Intensity-Based Registration and Feature-Based Registration for Neurointerventions", Robert A. McLaughlin, et al., MICCAI 2002, LNCS 2489, pp. 517-524.

"Edge Detection Using Contour Tracing", Delp & Chu, 47 (Center for Robotics and Integrated Manufacturing), Jul. 1983, 49 pages.

"Automated Skull Tracking for the CyberKnife® Image-guided Radiosurgery System", Dongshan Fu et al., Medical Imaging 2005: Visualization, Image-Guided Procedures, and Display, Proc. Of SPIE vol. 5744, pp. 366-377.

A Comparison of Similarity Measures for Use in 2-D-3-D Medical Image Registration, Graeme P. Penney et al., IEEE Transactions on Medical Imaging, vol. 17, No. 4, Aug. 1998, pp. 586-595.

* cited by examiner

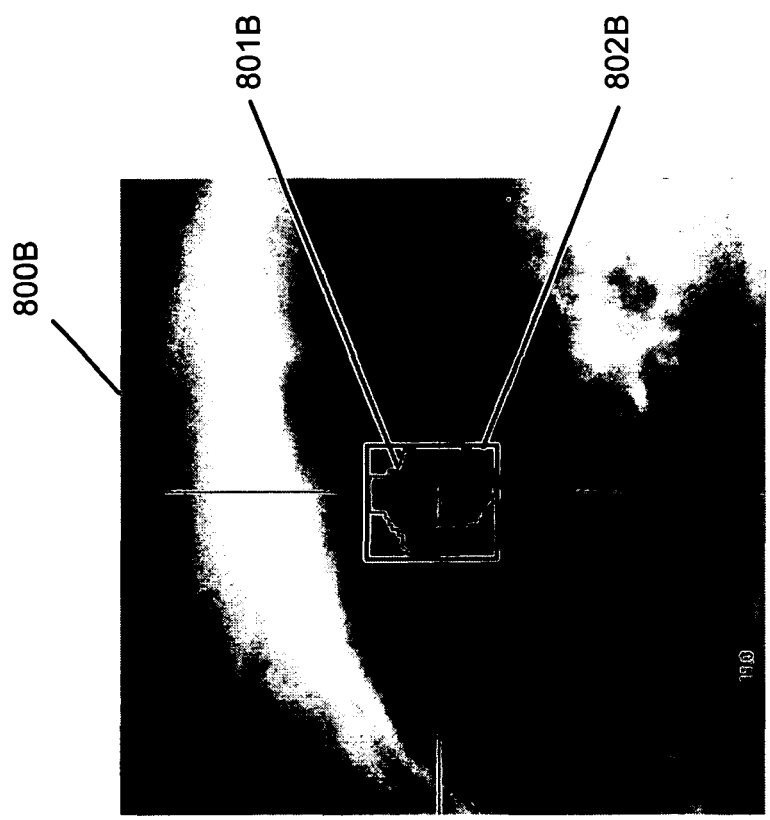
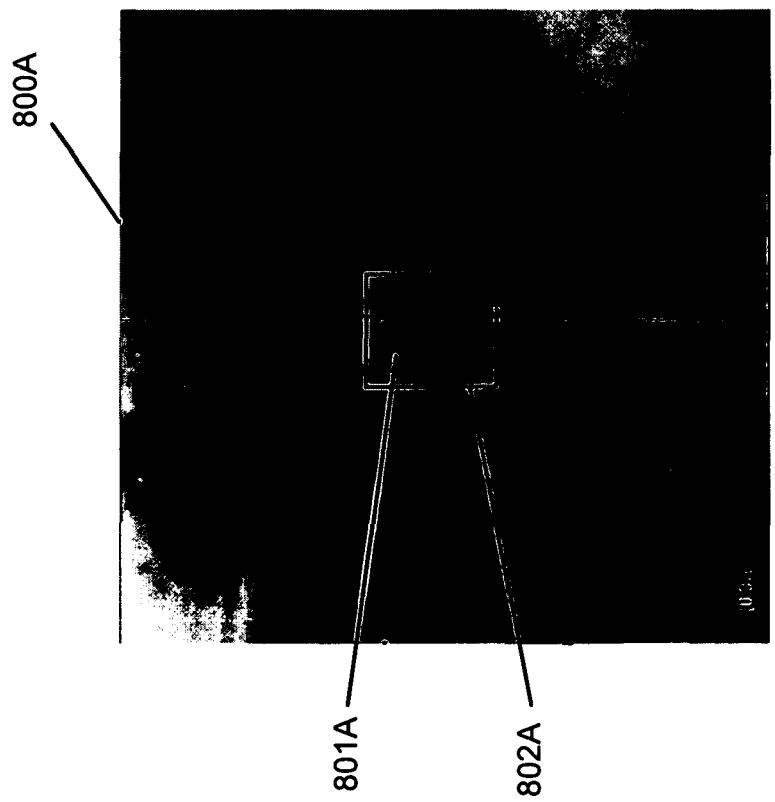
Figure 8B
Figure 8A

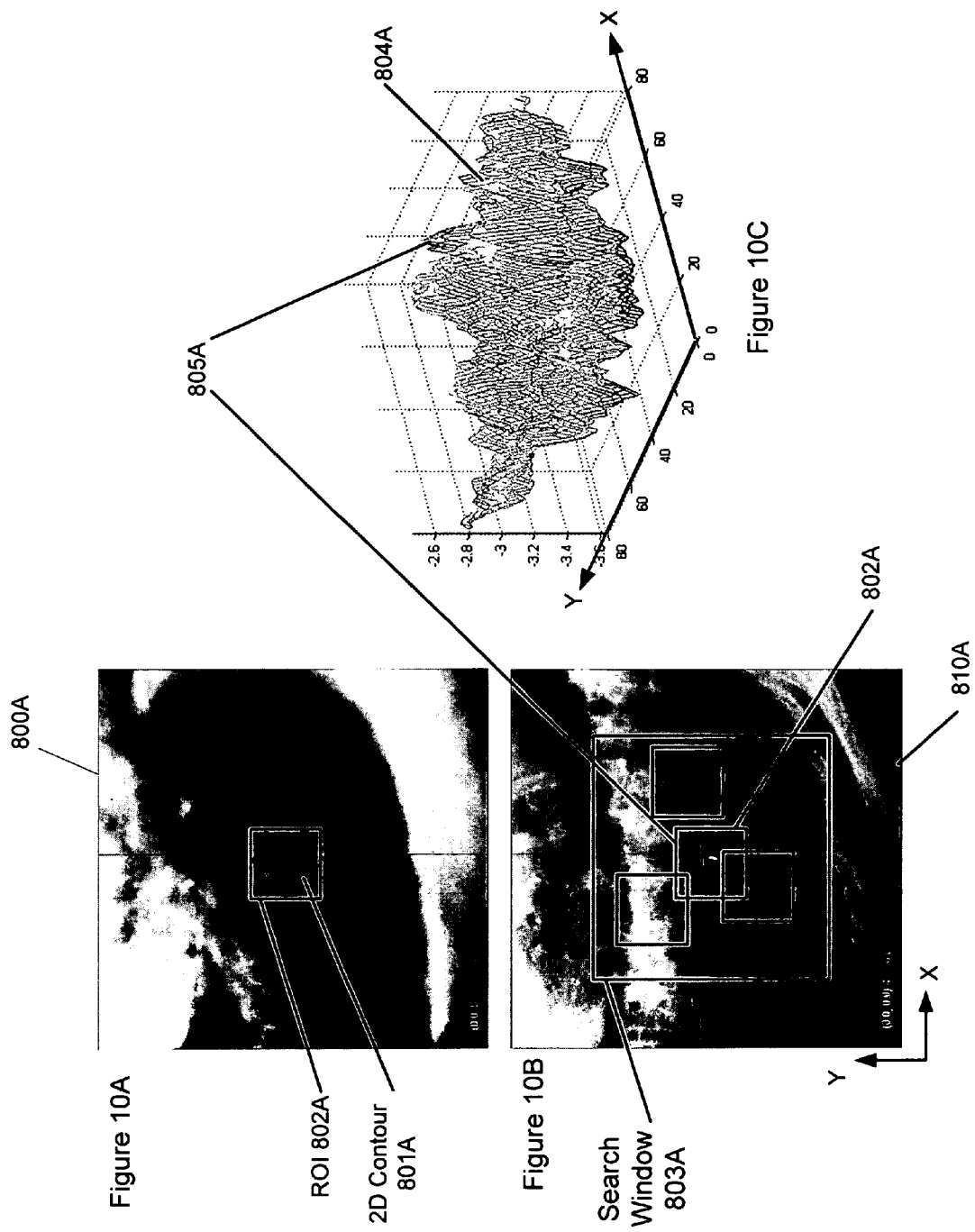

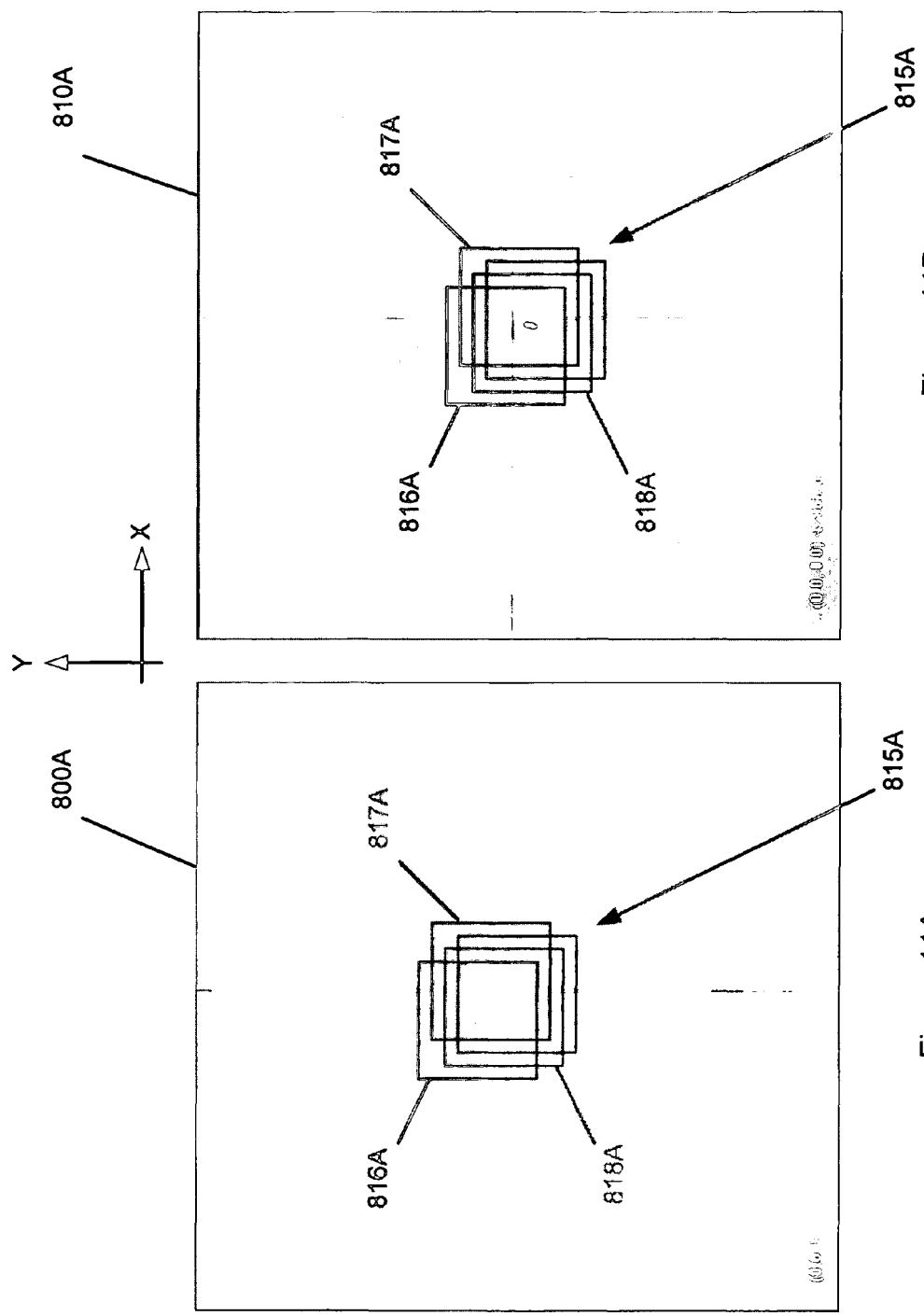

TARGET TRACKING USING DIRECT TARGET REGISTRATION

TECHNICAL FIELD

Embodiments of the invention are related to image-guided radiation treatment systems and, in particular, to tracking moving radiation targets during radiation treatment.

BACKGROUND

Pathological anatomies such as tumors and lesions can be treated with an invasive procedure, such as surgery, which can be harmful and full of risks for the patient. A non-invasive method to treat a pathological anatomy (e.g., tumor, lesion, vascular malformation, nerve disorder, etc.) is external beam radiation therapy. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to the tumor. As a result, the cumulative radiation dose at the tumor is high and the average radiation dose to healthy tissue is low.

The term "radiotherapy" refers to a procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centiGray (cGy)), short treatment times (e.g., 10 to 30 minutes per treatment) and hyperfractionation (e.g., 30 to 45 days of treatment). For convenience, the term "radiation treatment" is used herein to mean radiosurgery and/or radiotherapy unless otherwise noted.

Image-guided radiotherapy and radiosurgery systems include gantry-based systems and robotic-based systems. In gantry-based systems, a radiation source is attached to a gantry that moves around a center of rotation (isocenter) in a single plane. The radiation source may be rigidly attached to the gantry or attached by a gimbaled mechanism. Each time a radiation beam is delivered during treatment, the axis of the beam passes through the isocenter. Treatment angles are therefore limited by the rotation range of the radiation source and the degrees of freedom of a patient positioning system. In robotic-based systems, such as the CYBERKNIFE® Stereotactic Radiosurgery System manufactured by Accuray Incorporated of California, the radiation source is not constrained to a single plane of rotation and has five or more degrees of freedom.

In conventional image-guided radiation treatment systems, patient tracking during treatment is accomplished by comparing two-dimensional (2D) in-treatment x-ray images of the patient to 2D digitally reconstructed radiographs (DRRs) derived from the three dimensional (3D) pre-treatment imaging data that is used for diagnosis and treatment planning. The pre-treatment imaging data may be computed tomography (CT) data, magnetic resonance imaging (MRI) data, positron emission tomography (PET) data or 3D rotational angiography (3DRA), for example. Typically, the in-treatment x-ray imaging system is stereoscopic, producing images of the patient from two or more different points of view (e.g., orthogonal).

A DRR is a synthetic x-ray image generated by casting (mathematically projecting) rays through the 3D imaging data, simulating the geometry of the in-treatment x-ray imaging system. The resulting DRR then has the same scale and point of view as the in-treatment x-ray imaging system, and can be compared with the in-treatment x-ray imaging system to determine the location of the patient. To generate a DRR, the 3D imaging data is divided into voxels (volume elements) and each voxel is assigned an attenuation (loss) value derived from the 3D imaging data. The relative intensity of each pixel in a DRR is then the summation of the voxel losses for each ray projected through the 3D image. Different patient poses are simulated by performing 3D transformations (rotations and translations) on the 3D imaging data before the DRR is generated.

In some image-guided systems, the 3D transformations and DRR generation are performed iteratively in real time, during treatment. In other systems, such as the CYBERKNIFE® Stereotactic Radiosurgery System manufactured by Accuray Incorporated of Sunnyvale, Calif., a set of DRRs (in each projection) corresponding to an expected range of patient poses may be pre-computed before treatment begins.

Each comparison of an in-treatment x-ray image with a DRR produces a similarity measure or, equivalently, a difference measure (e.g., cross correlation, entropy, mutual information, gradient correlation, pattern intensity, gradient difference, image intensity gradients) that can be used to search for a 3D transformation that produces a DRR with a higher similarity measure to the in-treatment x-ray image (or to search directly for a pre-computed DRR as described above). When the similarity measure is sufficiently maximized (or equivalently, a difference measure is minimized), the 3D transformation corresponding to the DRR can be used to align the 3D coordinate system of the treatment plan with the 3D coordinate system of the treatment delivery system, to conform the relative positions of the radiation source and the patient to the treatment plan. In the case of pre-computed DRRs, the maximum similarity measure may be used to compute a differential 3D transformation between the two closest DRRs.

Image-guided radiation treatment systems provide an effective and non-invasive solution to the treatment of a wide variety of pathological anatomies (pathologies). However, certain types of pathologies present a particularly difficult treatment challenge. These types of pathologies may include relatively small tumors in relatively large organs such as the lungs, liver and pancreas, where the density of the tumor is very close to the density of the surrounding healthy tissue and the tumor is difficult to visualize using standard imaging technologies (e.g., x-ray imaging). Typically, these tumors are approximately 15 millimeters or less in diameter, but larger tumors may present the same or similar problems depending on the type of tumor and the specific organ. The challenge is particularly difficult when the tumor is in motion due to patient breathing during treatment, and the tumor must be tracked in real time or near real time.

One conventional method of dealing with the motion of a target region during radiation treatment involves the image tracking of fiducial markers that are placed in or near the target region. The position and motion of the fiducial markers is correlated with the position and motion of the target region so that real-time correction of the position of the treatment beam to follow the motion of the target region may be realized. This approach has the disadvantage of requiring an invasive surgical procedure to place the fiducial markers.

Conventional image-guided treatment systems attempt to locate pathologies using DRRs and in-treatment x-ray images with relatively large fields of view in an attempt to maximize image information. However, in the case of the small, poorly differentiated and moving pathologies discussed above, the conventional approach may be computationally expensive and time-consuming, slowing the imaging processing functions of the treatment system and rendering the output data rate too low for accurate tumor tracking.

BRIEF DESCRIPTION OF THE DRAWINGS

The present invention is illustrated by way of example, and not by limitation, in the figures of the accompanying drawings in which:

FIGS. 8A and 8B illustrate regions of interest surrounding a radiation target in one embodiment;

FIG. 10A illustrates a 2D contoured lung tumor and a region of interest in the first projection of FIG. 8A in one embodiment;

FIG. 10B illustrates a search window in an in-treatment x-ray image in the first projection of the volume of interest of FIG. 10A;

FIG. 10C illustrates the value of a similarity measure as a function of the location of a region of interest within a search window in one embodiment;

FIGS. 11A and 11B illustrate shift correlation windows corresponding to correct tumor detection in one embodiment;

DETAILED DESCRIPTION

Figure 1A:
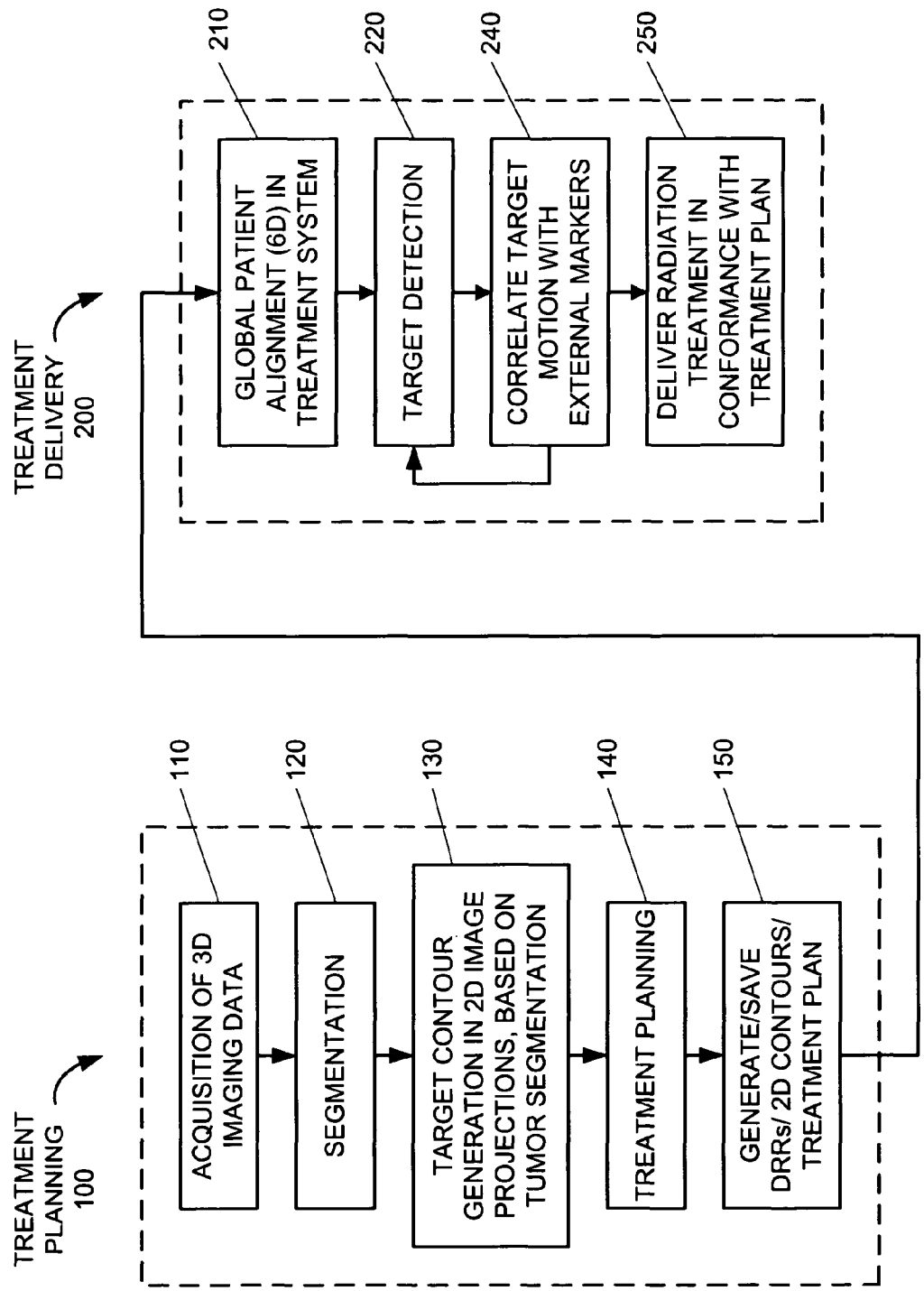
FIG. 1A is a flowchart illustrating an overview of treatment planning and treatment delivery processes in which embodiments of the invention may be implemented.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of a radiosurgery or radiotherapy procedure, which may include times when the radiation source is either on or off. From time to time, for convenience of description, CT imaging data may be used herein as an exemplary 3D imaging modality. It will be appreciated that data from any type of 3D imaging modality such as CT data, MRI data, PET data, 3DRA data or the like may also be used in various embodiments of the invention.

Unless stated otherwise as apparent from the following discussion, it will be appreciated that terms such as "segmenting," "generating," "registering," "determining," "aligning," "positioning," "processing," "computing," "selecting," "estimating," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

Methods, apparatus and systems are described for detecting and tracking a moving radiation target having motion in up to three translational directions, by using direct registration of the radiation target, to synchronize a radiation treatment source with the motion of the radiation target. Embodiments of the present invention make use of pre-treatment image enhancement techniques, known as 2-dimensional (2D) contouring, to define limited regions of interest around the contour of a radiation target (e.g., a lung tumor). These regions of interest are expressed in regions in DRRs of limited size which are matched to search windows of limited size in in-treatment x-ray images in order to locate the radiation target. The limited sizes of the regions of interest in the DRRs and the search windows in the in-treatment x-ray images may reduce the computational task of image registration and increase the speed of target detection. The reduced computation time may also free processing time for the computation of detection quality measures, which provide a quality assurance step for the detection of low contrast targets. Embodiments of the invention may be described with respect to a particular type of pathological anatomy such as a lung tumor, for ease of discussion. In alternative embodiments, the techniques described herein may be used to detect and track other types of pathological anatomies in other organs (e.g., liver, pancreas, etc.).

FIG. 1A is a flowchart illustrating an overview of treatment planning and treatment delivery processes, in one embodiment, which will be described in greater detail below. In FIG. 1A, treatment planning 100 begins with the acquisition of 3D imaging data (operation 110) from a 3D imaging system such as a CT scanner, MRI scanner, etc. Segmentation of the 3D imaging data (operation 120) is performed to define and identify the boundaries of the radiation target, critical structures to avoid during treatment and/or bony structures such as the spine or cranium that may be used for patient alignment during treatment.

The next operation (operation 130) is the generation of contours of the radiation target in 2D projections of the 3D imaging data that correspond to the projections of DRRs used during treatment delivery. Two-dimensional contouring methods are known in the art, and generally employ gray level edge detection with different types of spatial operators such as the Sobel operator and the Frei-Chen operator. Treatment planning (operation 140) is next performed by a medical physicist or other clinician to achieve a specified radiation dose to the radiation target, with a specified level of homogeneity and conformality, while keeping the radiation dose to healthy tissue and critical structures below specified levels. Once the treatment goals have been achieved in the plan, sets of DRRs are generated that correspond to the expected positions of the patient during treatment, and the treatment plan and DRRs are saved (operation 150). In other embodiments, DRRs may be generated in real time during radiation treatment. In one embodiment, sets of DRRs may be generated from 3D imaging data having the spine and/or other bony structures removed to increase the visibility/contrast of the radiation target, if such structures would otherwise occlude or obscure the radiation target. Removal of these structures may be performed by manipulating voxel masks in the 3D imaging data as is known in the art. In one embodiment, sets of DRRs may be generated from the 3D imaging data with only the spine and, optionally, some surrounding tissue retained and with motion artifacts (e.g., breathing artifacts) removed, which may be used to enhance patient alignment as described below.

The treatment delivery process 200 begins with global patient alignment (pre-alignment) in the treatment system (operation 210), followed by target detection (operation 220), correlation of target motion with external markers (operation 240) and the delivery of radiation treatment in conformance with the treatment plan. These steps are expanded in FIG. 1B, and discussed below.

Figure 1B:
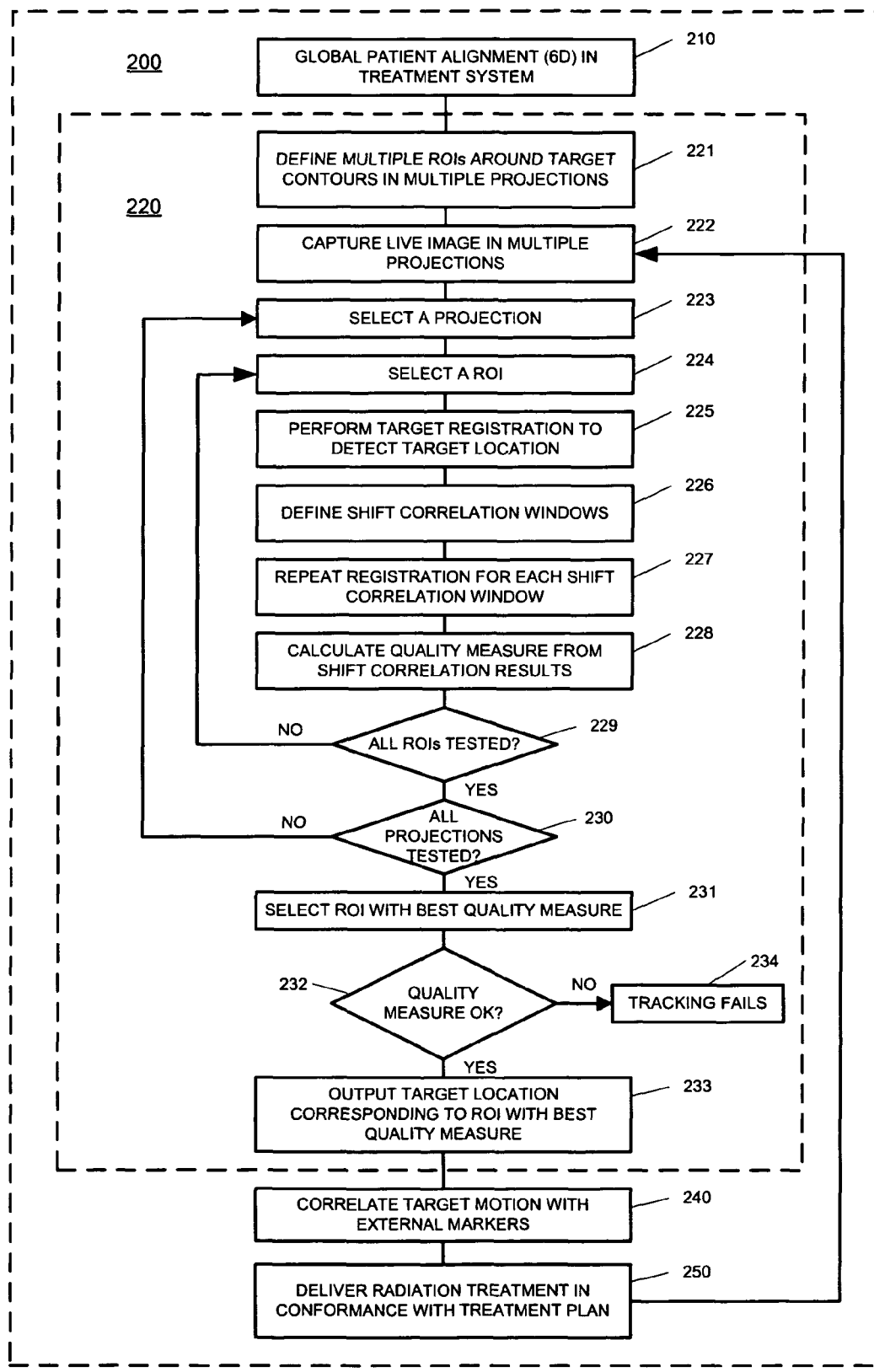
FIG. 1B is a flowchart illustrating radiation target detection in one embodiment.

Global patient alignment (operation 210) may be performed in six dimensions including three translations and three rotations, using DRRs and x-ray images of a large volume of interest, which may include identifiable landmarks such as fiducial markers and/or bony structures (e.g., the spine, the cranium) and/or pattern intensity variations that can be used for global alignment. Alternatively, the alignment may be performed using enhanced DRRs, such as those described above, containing segmented spine or other data. In different embodiments, global positioning may be performed by matching DRRs and x-ray images in one projection, two projections, or three or more projections depending on the geometry of the in-treatment imaging system Once initial global positioning has been achieved, radiation target detection (operation 220) may be performed. In one embodiment, as illustrated in FIG. 1B, target detection may include the following steps, which are described in greater detail hereafter:

1. Defining multiple regions of interest (ROI) around the 2D contours of the radiation target in multiple projections (operation 221).

2. Capturing live (e.g., in-treatment x-ray) images of the volume of interest containing the radiation target (operation 222)

3. Selecting a projection (operation 223).

4. Selecting a ROI in the selected projection (operation 224).

5. Performing target registration to locate the radiation target (operation 225);

6. Defining a number of shift correlation windows, offset from the selected ROI (operation 226);

7. Repeating and correlating target registration for each shift correlation window (operation 227);

8. Calculating a quality measure from the shift correlation results (operation 228);

9. Repeating operations 224-228 until all of the ROIs in the selected projection have been tested (operation 229);

10. Repeating operations 223-229 until all of the ROIs in all projections have been tested (operation 230).

11. Selecting the ROI with the best quality measure (operation 231);

12. Determining if the quality measure is good enough for treatment delivery (operation 232) and, if the quality measure is good enough, then:

13. Outputting the target location of the selected ROI for treatment delivery (operation 233). But, if the quality measure is not good enough, determining that target tracking has failed (operation 234).

If target detection is successful, then the treatment delivery process continues at operation 240 by correlating the location of the target with external markers on the patient (which may be visually tracked by an independent optical tracking system (e.g., a laser tracking system) and initiating the capture of another set of live images. Operations 220 and 240 may be repeated, tracking the radiation target until a correlation model is developed between the movement of the external markers and the detected locations of the radiation target. Operations 220 and 240 may also be repeated to update the correlation model.

Figure 2:
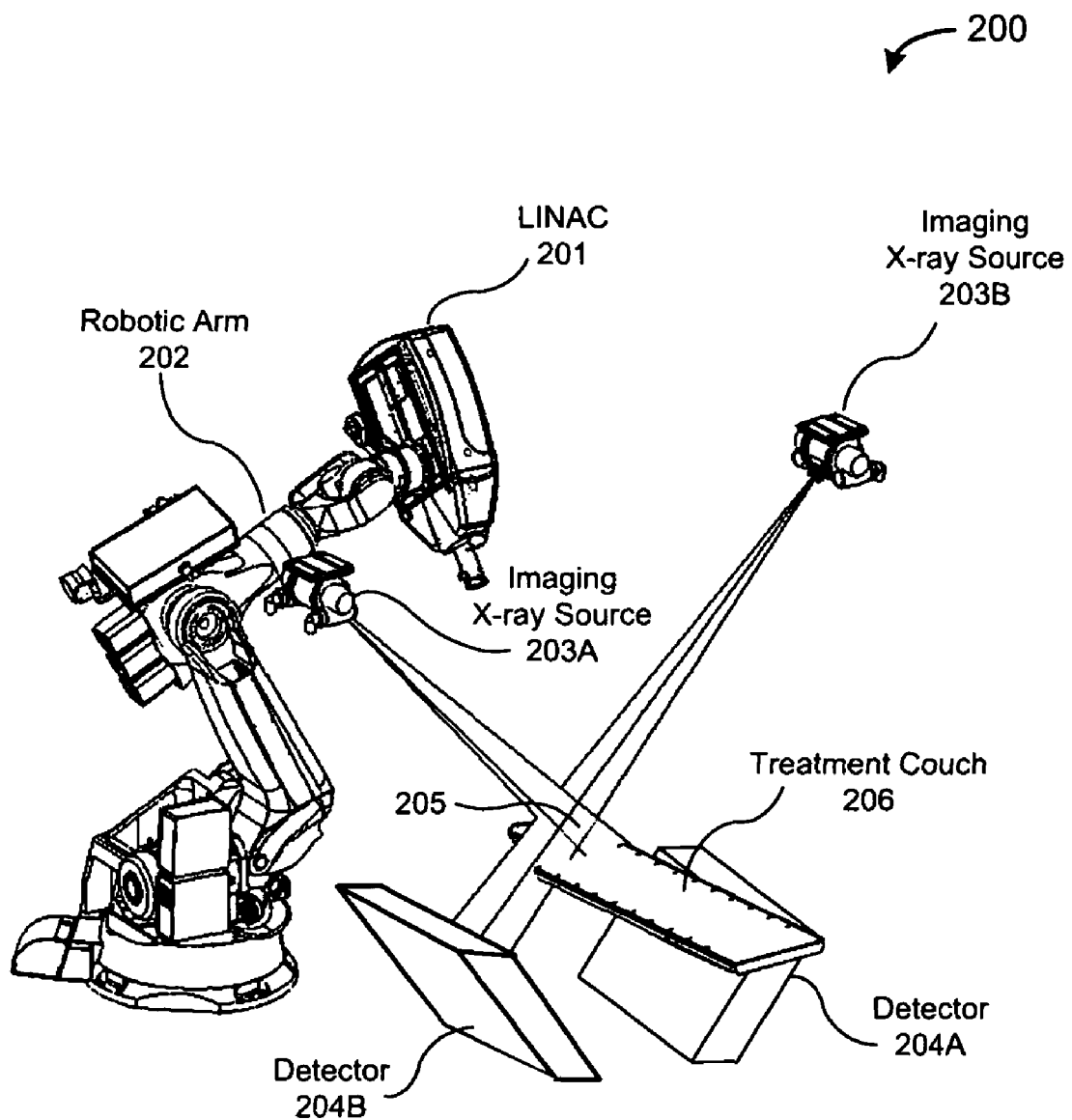
FIG. 2 illustrates an image-guided robotic radiosurgery system in one embodiment.

FIG. 2 illustrates the configuration of an image-guided, robotic-based radiation treatment system 200, such as the CYBERKNIFE® Stereotactic Radiosurgery System manufactured by Accuray Incorporated of Sunnyvale, Calif., that may be used to implement embodiments of the invention. In FIG. 2, the radiation treatment source is a linear accelerator (LINAC) 201 mounted on the end of a robotic arm 202 having multiple (e.g., 5 or more) degrees of freedom in order to position the LINAC 201 to irradiate a pathological anatomy (target region or volume) with beams delivered from many angles, in many planes, in an operating volume around the patient. Treatment may involve beam paths with a single isocenter, multiple isocenters, or with a non-isocentric approach.

The treatment delivery system of FIG. 2 includes an in-treatment imaging system, which may include x-ray sources 203A and 203B and x-ray detectors (imagers) 204A and 204B. The two x-ray sources 203A and 203B may be mounted in fixed positions on the ceiling of an operating room and may be aligned to project imaging x-ray beams from two different angular positions (e.g., separated by 90 degrees) to intersect at a machine isocenter 205 (which provides a reference point for positioning the patient on a treatment couch 206 during treatment) and to illuminate imaging planes of respective detectors 204A and 204B after passing through the patient. In other embodiments, system 200 may include more or less than two x-ray sources and more or less than two detectors, and any of the detectors may be movable rather than fixed and/or mounted below floor level. In yet other embodiments, the positions of the x-ray sources and the detectors may be interchanged.

Treatment Planning

As noted above, the first step in treatment planning 100, after acquisition of the 3D imaging data is segmentation (operation 120). Medical image segmentation is the process of partitioning a 3D medical image (such as a CT, MRI, PET or 3DRA image) into regions that are homogeneous with respect to one or more characteristics or features (e.g., tissue type, density). In radiation treatment systems (including both frame-based and image-guided), segmentation is a step in treatment planning where the boundaries and volumes of a targeted pathological anatomy (e.g., a tumor or lesion) and critical anatomical structures (e.g., spinal chord) are defined and mapped into the treatment plan. The precision of the segmentation may be critical to obtaining a high degree of conformality and homogeneity in the radiation dose during treatment of the pathological anatomy while sparing healthy tissue from unnecessary radiation.

Figure 5B:
FIGS. 5A and 5B illustrate spine segmentation and removal in one embodiment.
Figure 5A:

As noted above, segmentation may be used to manipulate 3D image data to remove unwanted features or artifacts for improved image registration. FIGS. 5A and 5B illustrate one example. FIG. 5A illustrates a DRR in one projection that is generated from an unmodified 3D image file. In contrast, FIG. 5B illustrates a DRR generated from the same 3D image file after spine segmentation and elimination of non-spinal features. In certain embodiments, this type of DRR may be used to enhance the initial global alignment of a patient within a treatment system (e.g., when fiducial markers have not been used).

Figure 6C:
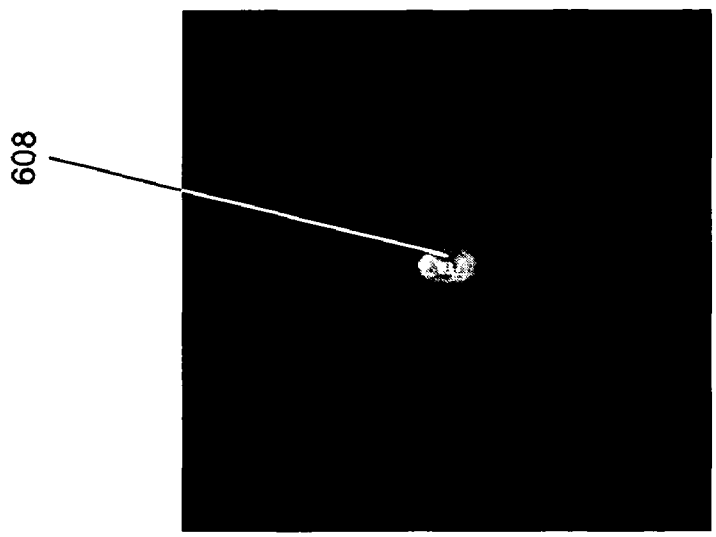
FIGS. 6A-6C illustrate tumor visualization and segmentation in one embodiment.
Figure 6A:
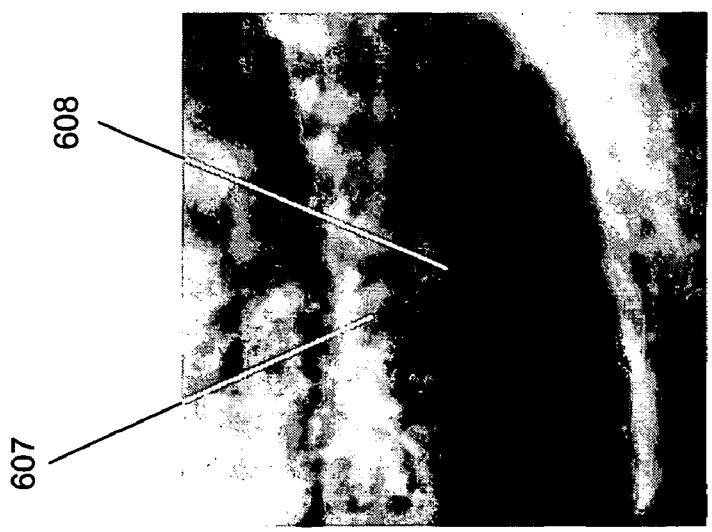
Figure 6B:
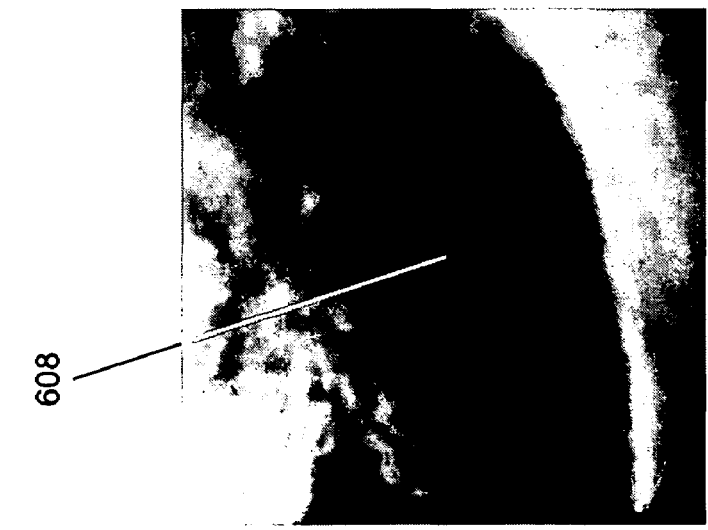

FIGS. 6A and 6B illustrate a different use of segmentation. FIG. 6A illustrates a DRR from unmodified 3D scan data, where features of the spine 607 overlap the boundaries of a lung tumor 608, making it difficult to define the tumor contour. In FIG. 6B, the spine has been segmented and deleted from the 3D scan data to produce a DRR with the tumor better visualized. FIG. 6C illustrates how the tumor may also be segmented for 2D contour generation, as described below.

The processes described above may be automated by a segmentation tool, such as the tool provided in the Multi-Plan™ treatment planning system available from Accuray Incorporated of Sunnyvale, Calif. The segmentation tool may be used to manipulate a patient's medical image (e.g., CT or other image volume such as MRI, PET, etc.). Alternatively, other tools may be used.

Figure 6D:
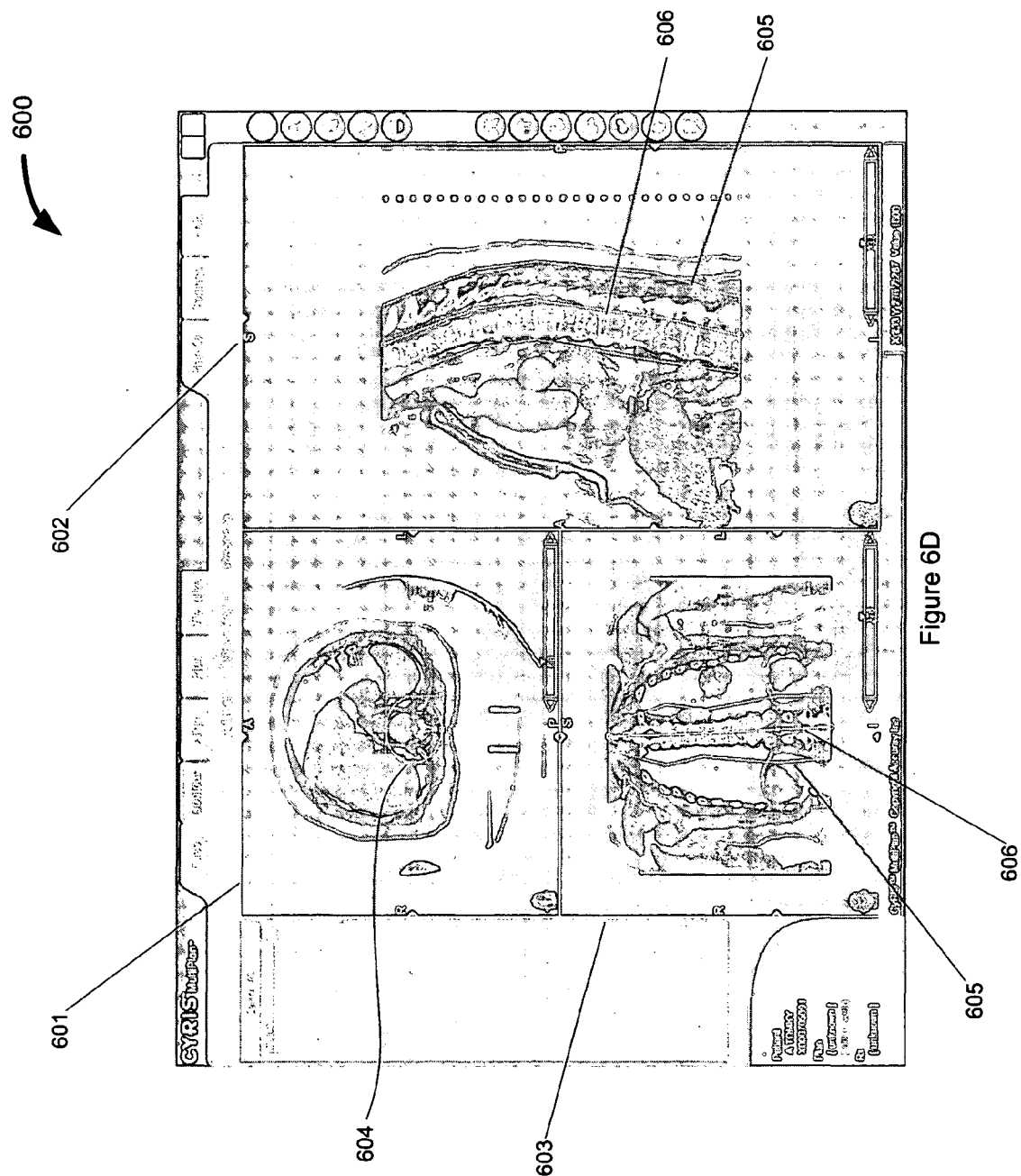
FIG. 6D illustrates a segmentation tool in one embodiment.

FIG. 6D is a screenshot 600 illustrating how the segmentation tool allows a user to delineate a spine in the volume of interest simultaneously from three cutting planes of the medical image: the axial plane 601, the sagittal plane 602 and the coronal plane 603.

On the axial plane 601, a two-dimensional contour is displayed. The contour can be a solid contour when it is defined by a user, or it can be a dashed-line contour interpolated from adjacent contours by a computer. A user can modify the contour by resizing it, scaling it or moving it.

On the sagittal plane 602 and coronal plane 603, a projected silhouette contour 605 of the spine volume of interest is displayed. The centers of all user defined contours (such as contour 604, for example) are connected as the central axis of the spine 606. A user can move, add or remove contours by moving or dragging the centers of the contours. When the center of a contour is moved on the sagittal or coronal planes, the actual contour defined on the axial image slice is moved accordingly. When the user selects any point in between two center points of adjacent axial contours, a new contour is added at that position, with the contour automatically set to the interpolation of the two adjacent axial contours. When a user drags and drops the center point of a contour outside the region of the two adjacent contours, or outside the image boundary, the contour is removed from the volume of interest. Once the spine is delineated and stored in the geometrical format, it is converted to the volume format as a three-dimensional image volume containing only the voxels associated with the spine.

Figure 7:
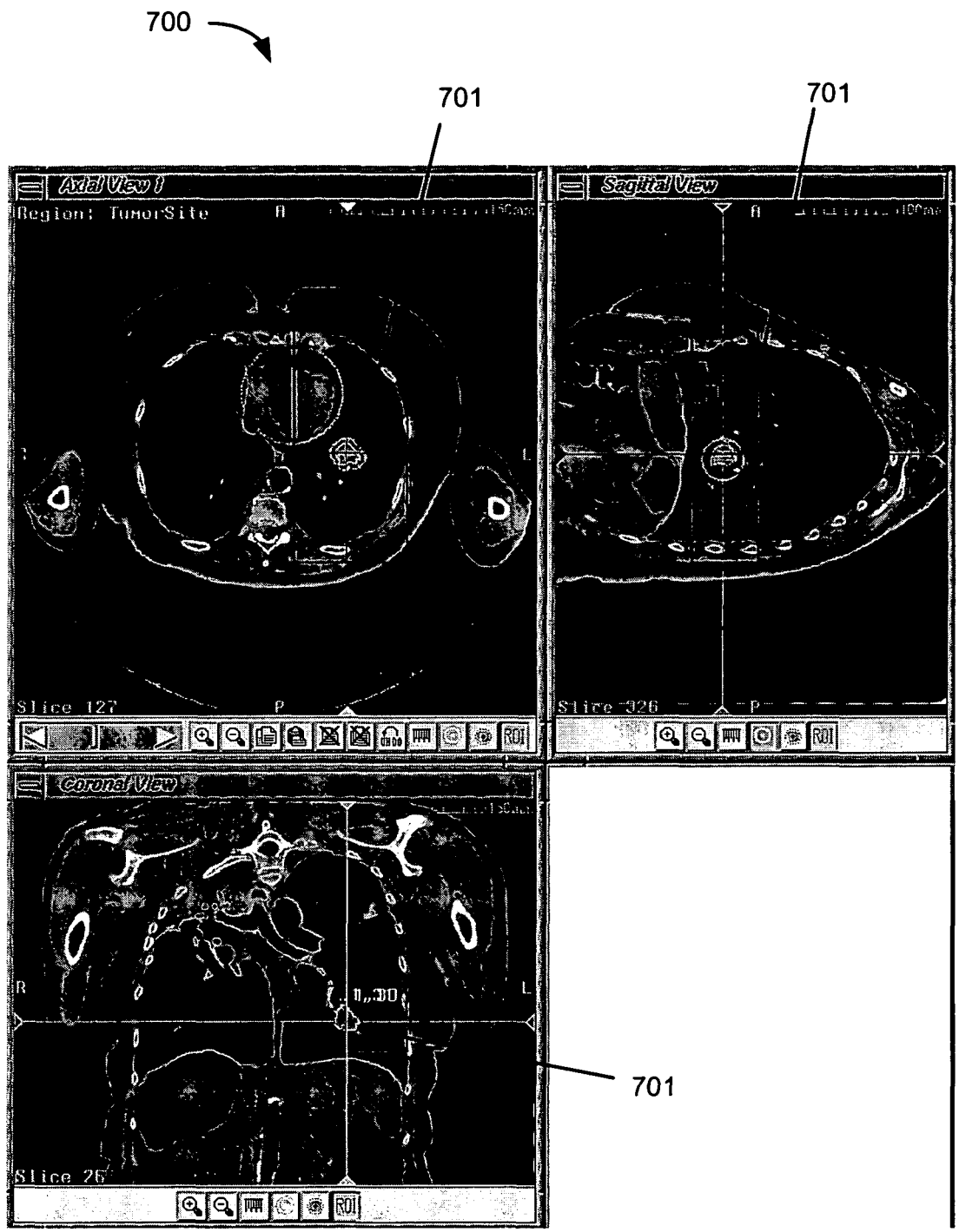
FIG. 7 illustrates segmentation of a lung tumor in a treatment planning system in one embodiment.

The next step in treatment planning in certain embodiments is the generation of 2D contours of the radiation target based on target segmentation (operation 130). FIG. 7 is a screenshot 700 of a CT image illustrating a lung tumor 701 in the aforementioned axial, sagittal and coronal planes (MRI or another non-x-ray imaging modality may be used in conjunction with CT data to visualize a tumor when the x-ray density of the tumor is very close to that of its surrounding tissue, as in the case of lung tumors). The same contouring tools described in respect to spine segmentation above may be used to segment the tumor in the 3D image and to provide data inputs to automatic 2D contour generation processes that may be used to create and overlay 2D tumor contours on DRRs during treatment delivery. Methods for automatically generating 2D contours (e.g., automatic edge detection) are known in the art and are described, for example, in Delp & Chu, *Edge Detection Using Contour Tracing*, 47 (Center for Robotics and Integrated Manufacturing) (1983).

The treatment planning process concludes with the development of the actual treatment plan, generating DRRs and saving (e.g., digitally) the plan, DRRs and 2D target contours for subsequent use in treatment delivery (operations 140 and 150). The details of operations 140 and 150 are known in the art and, accordingly are not described in detail.

Treatment Delivery

Global Alignment

Figure 3A:
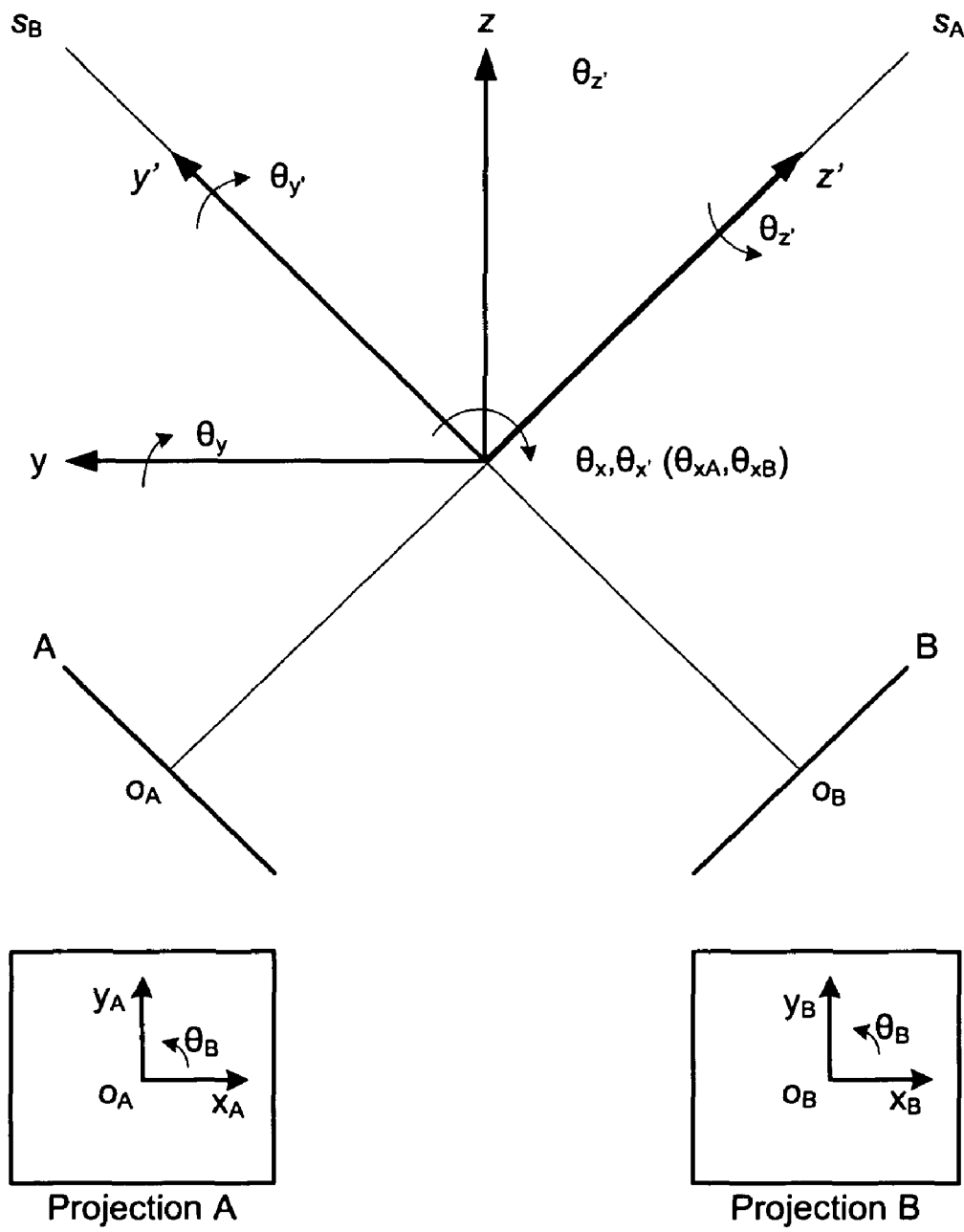
FIG. 3A illustrates imaging and treatment delivery coordinate systems in one embodiment.
Figure 3B:
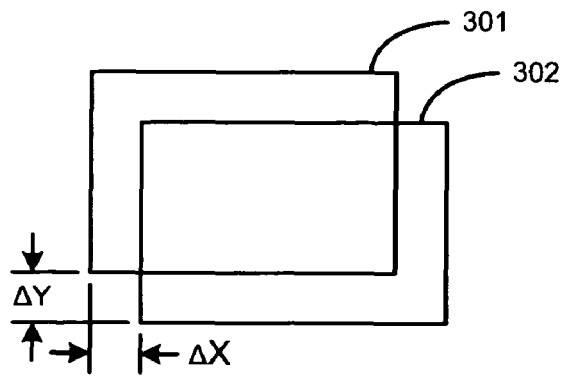
FIGS. 3B-3E illustrate 2D-2D registration of x-ray images and DRRs in one embodiment.
Figure 3C:
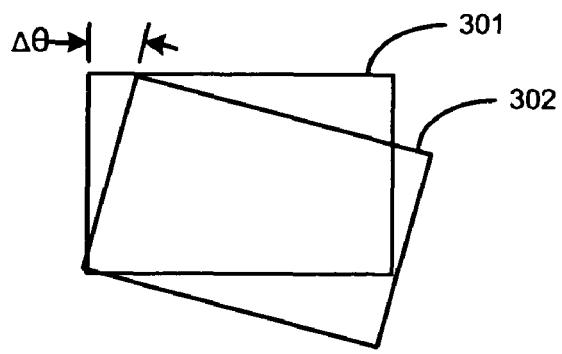
Figure 3D:
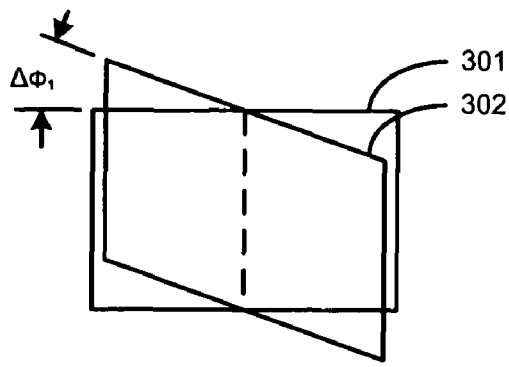
Figure 3E:
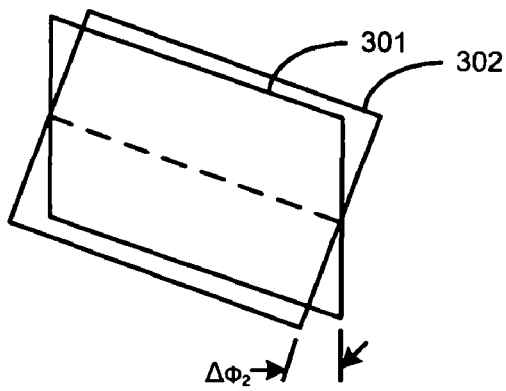

As noted above, the first step in treatment delivery is global patient alignment within the treatment delivery system (operation 210). As an aid to understanding the description of global alignment (pre-alignment) and target detection that follow, FIG. 3A illustrates the relationships among the 3D coordinate system of a treatment delivery system (such as treatment delivery system 200), the 2D coordinate system of an in-treatment imaging system (such as the in-treatment imaging system in treatment delivery system 200) and the 3D coordinate system of a 3D image (e.g., CT, MRI, PET, etc.). In FIG. 3A, the coordinate system xyz (where x is normal to, and pointing into, the plane of FIG. 3A) is associated with the 3D coordinates of a pre-treatment image, the coordinate system x'y'z' (where x' is normal to, and pointing into, the plane of FIG. 3A) is associated with the treatment delivery system, and the projections A and B are associated with the in-treatment imaging system where $S_A$ and $S_B$ represent x-ray sources (such as x-ray sources 103A and 103B) and $O_A$ and $O_B$ are the centers of the imaging planes of x-ray detectors (such as x-ray detectors 104A and 104B). In FIG. 2, the projections A and B are viewed from the directions $O_A S_A$ and $O_B S_B$, respectively. It is these two 2D image projections which are compared against DRRs to achieve image registration and alignment, both for global patient positioning and for embodiments of radiation target tracking described herein.

A 3D transformation may be defined from coordinate system xyz to coordinate system x'y'z' in FIG. 3A in terms of three translations ($\Delta x, \Delta y, \Delta z$) and three rotations ($\Delta\theta_x, \Delta\theta_y, \Delta\theta_z$). A 3D rigid transformation between the two 3D coordinate systems can be derived from basic trigonometry as:

$$x = x', \ y = (y' - z')/\sqrt{2}, \ z = (y' + z')/\sqrt{2}, \quad (1)$$
$$\theta_x = \theta_{x'}, \ \theta_y = (\theta_{y'} - \theta_{z'})/\sqrt{2}, \ \theta_z = (\theta_{y'} + \theta_{z'})/\sqrt{2}.$$

In the 2D coordinate system ($x_A, y_A$) for projection A, the 3D rigid transformation may be decomposed into the in-plane transformation ($\Delta x_A, \Delta y_A, \Delta\theta_A$) and two out-of-plane rotations ($\Delta\theta_{x_A}, \Delta\theta_{y'}$). Similarly, in the 2D coordinate system ($x_B, y_B$) for projection B, the decomposition consists of the in-plane transformation ($\Delta x_B, \Delta y_B, \Delta\theta_B$) and two out-of-plane rotations ($\Delta\theta_{x_B}, \Delta\theta_{z'}$). FIGS. 3B through 3E illustrate the in-plane transformations and out-of-plane rotations described herein, where a 2D x-ray image is represented by plane 301 and the 2D DRR is represented by plane 302. The 3D rigid transformation of equation (1) may be simplified by noting that the use of two projections over-constrains the solution to the six parameters of the 3D rigid transformation. The translation $x_A$ in projection A is the same parameter as $x_B$ in projection B, and the out-of-plane rotation $\theta_{x_A}$ in projection A is the same as $\theta_{x_B}$ in projection B. If $\alpha_A$ and $\alpha_B$ are geometric amplification factors (e.g., scale factors related to source-to-patient and patient-to-detector distances) for projections A and B, respectively, then the translations between the coordinate system (x'y'z') and the 2D coordinate systems have the following relationships:

$$\Delta x' = (\alpha_B \Delta x_B - \alpha_A \Delta x_A)/2, \ \Delta y' = \alpha_A \Delta y_A, \ \Delta z' = \alpha_B \Delta y_B. \quad (2)$$

For projection A, given a set of DRR images that correspond to different combinations of the two out-of-plane rotations ($\Delta\theta_{x_A}, \Delta\theta_{y'}$), the 2D in-plane transformation ($\Delta x_A, \Delta y_A, \Delta\theta_A$) may be estimated by a 2D to 2D image comparison, and the two out-of-plane rotations ($\Delta\theta_{x_A}, \Delta\theta_{y'}$) may be calculated by matching the x-ray image to the set of DRR images as described below, using similarity measures. Likewise, the same process may be used to solve the 2D in-plane transformation ($\Delta x_B, \Delta y_B, \Delta\theta_B$) and the out-of-plane rotations ($\Delta\theta_{x_B}, \Delta\theta_{z'}$) for the projection B. As described below, the in-plane transformation and out-of-plane rotations may be obtained by registration between the x-ray image and the set of DRR images, independently for both projection A and projection B. When a DRR image with a matching out-of-plane rotation is identified, the in-plane rotation and the out-of-plane rotation have the following relationships:

$$\Delta\theta_{y'} = \Delta\theta_B, \ \Delta\theta_{z'} = \Delta\theta_A. \quad (3)$$

If the out-of-plane rotation $\theta_{y'}$ is ignored in the set of reference DRR images for projection A, the in-plane transformation can be approximately described by $\Delta(x_A, \Delta Y_A, \Delta\theta_A)$ when $\Delta\theta_{y'}$ is small (e.g., less than 5°). Once this simplifying assumption is made, and given the set of reference DRR images which correspond to various out-of-plane rotations $\Delta\theta_{x_A}$, the in-plane transformation ($\Delta x_A, \Delta y_A, \Delta\theta_A$) and the out-of-plane rotation $\Delta\theta_{x_A}$ may be found by one or more search methods as are known in the art. These methods generally employ the calculation of a similarity measure, followed by the application of a gradient search algorithm to maximize the similarity between the in-treatment x-ray images and selected DRRs. Examples of similarity measures include (but are not limited to) normalized cross-section, entropy of the difference image, mutual information, gradient correlation, pattern intensity and gradient difference. A corresponding simplification may be made for projection B.

Given the results ($\Delta x_A, \Delta y_A, \Delta\theta_A, \Delta\theta_{x_A}$) in projection A and ($\Delta x_B, \Delta y_B, \Delta\theta_B, \Delta\theta_{x_B}$) in projection B, the approximation of the 3D rigid transformation in the 3D image coordinate system may be obtained using the following expressions $$\Delta x = (-\alpha_A \Delta x_A + \alpha_B \Delta x_B)/2, \ \Delta y = (\alpha_A \Delta y_A - \alpha_B \Delta y_B)/\sqrt{2}, \quad (4)$$
$$\Delta z = (\alpha_A \Delta y_A + \alpha_B \Delta y_B)/\sqrt{2}, \ \Delta\theta_x = (\Delta\theta_{x_A} + \Delta\theta_{x_B})/2,$$
$$\Delta\theta_y = (\Delta\theta_B - \Delta\theta_A)/\sqrt{2}, \ \Delta\theta_z = (\Delta\theta_B + \Delta\theta_A)/\sqrt{2}.$$

Thus, the 3D transformation required to align the 3D coordinate system of the patient in the treatment delivery system with the coordinate system of a 3D treatment plan may be completely defined by the two sets of four parameters ($\Delta x_A, \Delta y_A, \Delta\theta_A, \Delta\theta_{x_A}$) and ($\Delta x_B, \Delta y_B, \Delta\theta_B, \Delta\theta_{x_B}$).

Figure 4:
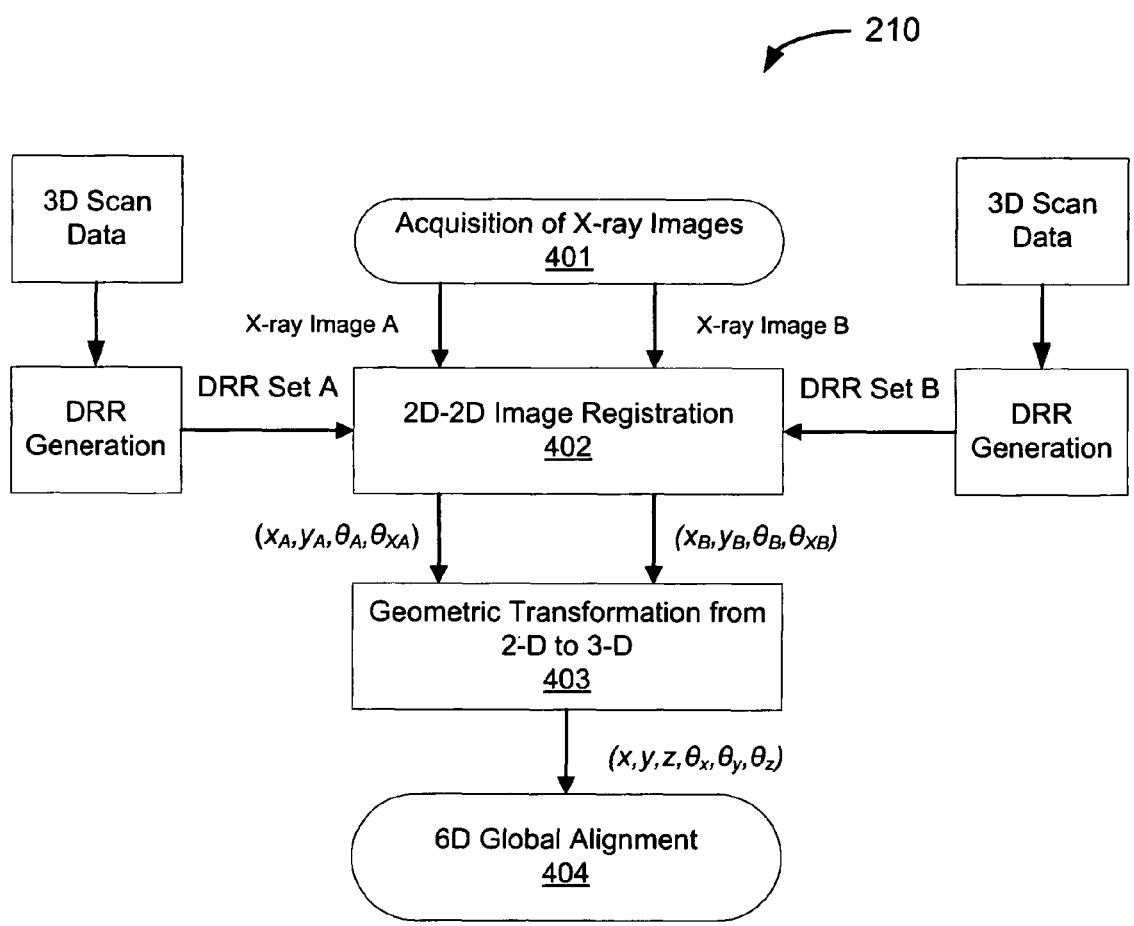
FIG. 4 is a flowchart illustrating global patient alignment in one embodiment.

The process of global alignment (operation 210) is illustrated schematically in FIG. 4. The process begins with the acquisition of in-treatment x-ray images (operation 401). In operation 402, the x-ray images are compared and registered, as described above, with DRR sets created from 3D scan data and imported from a treatment planning system. The results of the registration are the 2 sets of 2D transformation parameters that are used in operation 403 to calculate the 3D transformation required in operation 404 to bring the patient into alignment.

One result of the global alignment process is that in the subsequent operation of target detection (operation 220), searching is limited to two in-plane translations (x,y) in each projection because the 6D global alignment process eliminates in-plane and out-of-plane rotational errors. It will be appreciated that the geometric transformations described above may be applied to imaging systems having more than two imaging projections (e.g., three or more) by computing transformations for any pair of imaging projections.

Target Detection

Figure 9:
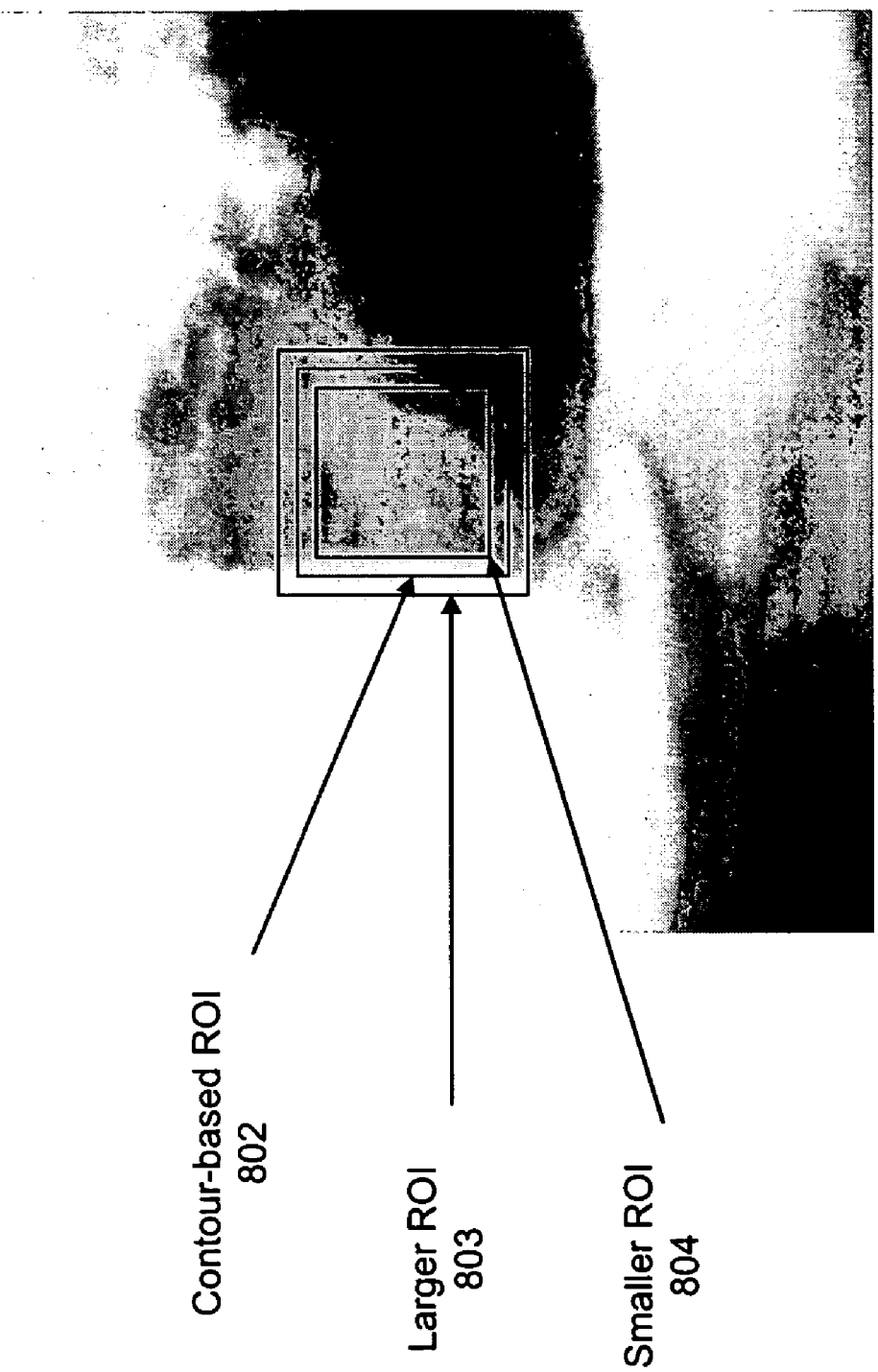
FIG. 9 illustrates the generation of multiple ROIs in one embodiment.

With reference again to FIG. 1B, target detection (operation 220) begins with operation 221, the definition of multiple regions of interest (ROIs), in multiple projections corresponding to the in-treatment imaging system, around the 2D contours of the radiation target created during treatment planning. This process is illustrated in FIGS. 8A, 8B and 9 for the exemplary case of a lung tumor. FIGS. 8A and 8B illustrate, respectively, DRRs 800A and 800B in two projections (e.g., projections A and B) selected for direct target registration after the global patient alignment described above. In the examples shown, the DRRs have been synthesized from 3D image data with spine removed to enhance the contrast of the tumor. In FIG. 8A, a 2D tumor contour 801A has been overlaid on DRR 800A and an initial ROI 802A in projection A has been generated around tumor contour 801A. Similar, in FIG. 8B, a 2D tumor contour has been overlaid on DRR 800B and an initial ROI 802B in projection B has been generated around tumor contour 801B. These initial ROIs may be selected to conform closely to the dimensions of the tumor contours in the horizontal and vertical dimensions of their respective DRRs, such that the ROIs include the tumor contour and some tissue outside of the tumor contour.

After an initial ROI is defined, additional ROIs may be defined that include more area than the initial ROI and less area than the initial ROI, in order to provide the opportunity for better tumor detection. For example, if the borders of the tumor are ill-defined and/or difficult to image using any of the normal 3D imaging techniques, then the 2D contour of the tumor generated in the treatment planning stage may include either more or less than all of the tumor. As a result, different sized ROIs may produce better tumor detection and/or treatment. These different sized ROIs are illustrated in FIG. 9, where in addition to a contour-based ROI 802, a larger ROI 803 and a smaller ROI 804 have been defined. In other embodiments, more or less than three ROIs may be used at the discretion of a clinician. In one embodiment, the step sizes between ROIs may vary from approximately 1 mm to approximately 5 mm, depending on the size of the tumor. However, any step size may be selected at the discretion of a clinician.

In the next step of target detection, operation 222, a live image of the patient is captured in the multiple projections of the in-treatment imaging system. In operation 223, one of the projections is selected. In operation 224, one of the ROIs is selected for target detection. In operation 225, target registration is performed to detect the target location by overlaying the selected ROI (containing the DRR image of the target) on the corresponding in-treatment x-ray image (which reflects the globally pre-aligned patient as described above) and performing a search within a search window in the in-treatment x-ray image. In one embodiment, the search algorithm may be the same as that used for global alignment (e.g., computation of a similarity measure and gradient searches to maximize the similarity), but constrained to the area of the search window. In other embodiments, the search may be a deterministic search (e.g., a raster search) within the search window for a maximum similarity measure. In addition, the search may utilize multi-level matching, as described below, to speed up the registration process. FIGS. 10A-10C illustrate the process.

FIG. 10A is a reproduction of the segmented DRR 800A of FIG. 8A showing the 2D contour 801A and region of interest 802A. FIG. 10B illustrates the corresponding in-treatment x-ray image 810A in projection A having a search window 803A. In one embodiment, the area of the search window 803A may be selected to be in the range of two to four times the area of the region of interest 802A. In other embodiments, the area of the search window may be larger or smaller, as determined by a clinician based on experience and/or clinical data.

Figure 10D:
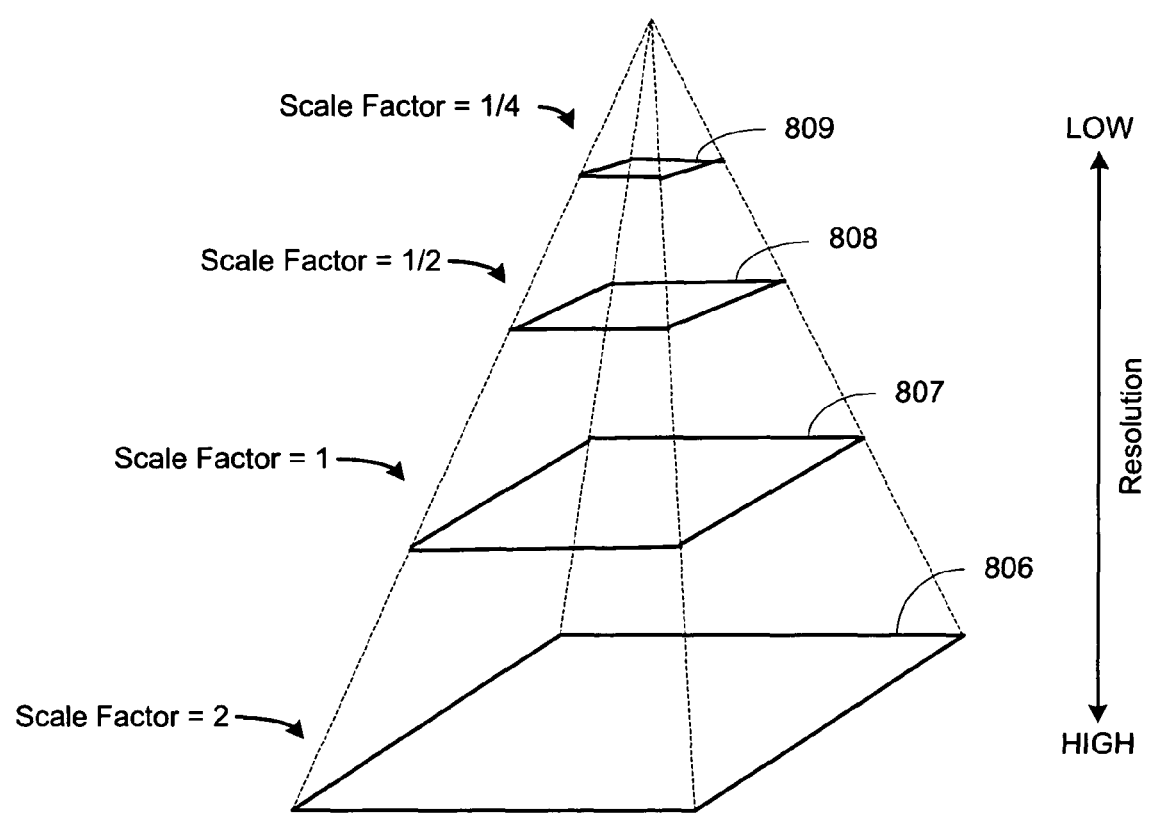
FIG. 10D illustrates multi-level matching in one embodiment.

Target detection may be performed by overlaying the region of interest 802A in the search window 803A of the in-treatment x-ray image 810A, moving the region of interest 802A within the search window 803A (as shown by the several example locations of region of interest 802A in search window 803A in FIG. 10B) and searching for a location that maximizes a similarity measure between the region of interest 802A and the portion of the search window 803A that the region of interest 802A overlaps. As illustrated in FIG. 10C, the movement of the region of interest within the search window describes a similarity measure surface 804A which has a maximum value 805A when the region of interest 802A is properly aligned with the tumor in the in-treatment x-ray image. A multi-level search may be used to reduce the probability that a search will get stuck at a local maximum of the similarity surface 804A, and not find the global maximum in the search window. As illustrated in FIG. 10D, an exemplary multi-level search begins at a low resolution search level 809 and proceeds to higher resolution levels 808, 807 and 806. At the lowest resolution level, 809, the dimensions of the selected ROI and the search window are reduced by a scale factor by sub-sampling. When the similarity measure is maximized at the lowest resolution, the results are passed to the next higher resolution level where the similarity measure is again maximized, and so on until the similarity measure is maximized at the highest resolution level. FIG. 10D illustrates one embodiment with four resolution levels where the resolution is doubled at each successive level. Other embodiments may use more or less than four levels and different resolution factors at each level.

Once the similarity measure is maximized, a quality measure may be determined. In operation 226, a first set of shift correlation windows is defined around the nominal location of the target as determined by the preceding search algorithm in operation 225. Each shift correlation window is offset from the nominal target location in different amounts, so that each shift correlation window contains different portions of the target and surrounding tissue. In operation 227, each shift correlation window is registered in the in-treatment x-ray image (e.g., as in operation 225) to find a second, matching set of shift correlation windows in the corresponding in-treatment x-ray image. FIG. 11A illustrates a first group of shift correlation windows 815A defined within the DRR 800A. The same group of shift correlation windows 815A is overlaid in the in-treatment x-ray image 810A in FIG. 11B.

If the initial target detection in operation 225 was correct, then the set of matching shift correlation windows in the in-treatment x-ray image will match the locations of the first set of shift correlation windows with little or no movement. That is, the final locations of each matching shift correlation window will be close to the initial locations of the first set of shift correlation windows when the best match has been achieved. Conversely, if the initial target detection was incorrect, then the final locations of the matching shift correlation windows may be significantly different from the initial locations of the first set of shift correlation windows when the best match has been achieved.

Figure 12A:
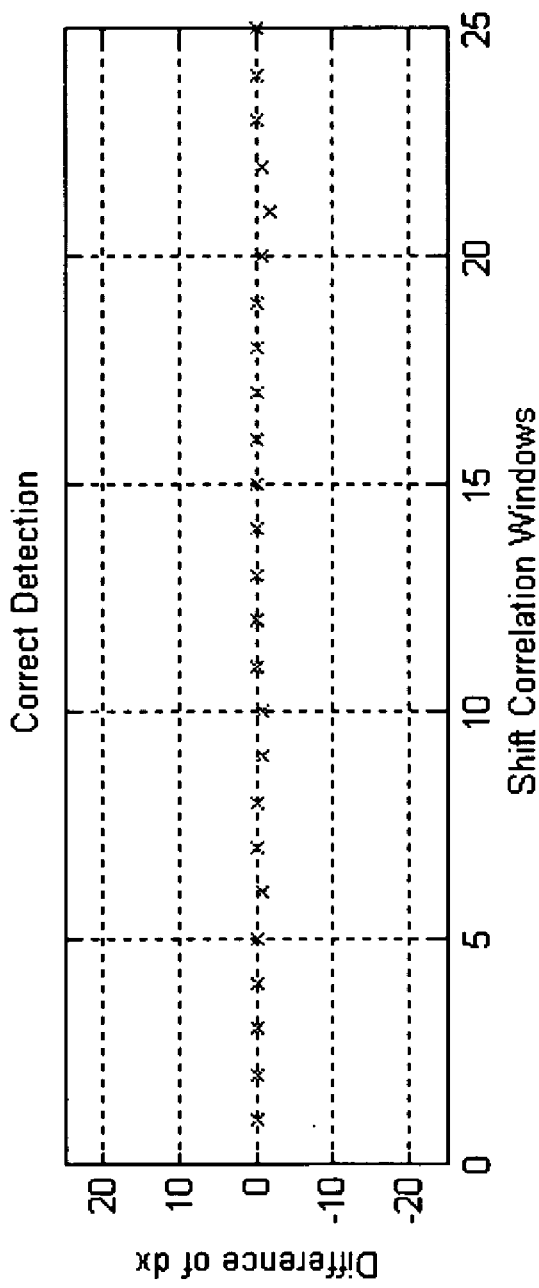
FIGS. 12A and 12B are graphs illustrating a quality measure for correct target detection in one embodiment.
Figure 12B:
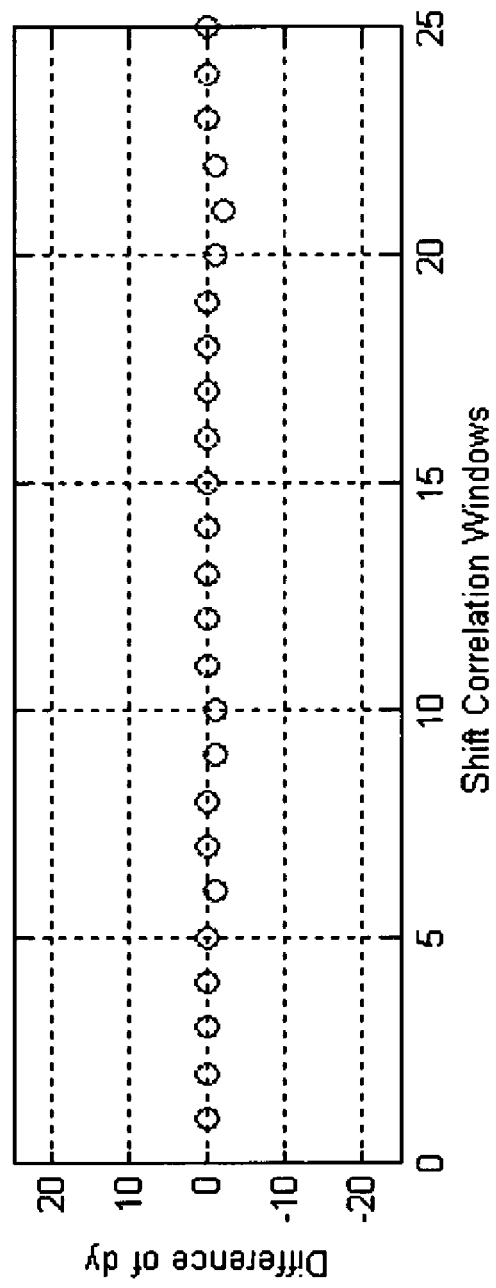

The difference between initial locations and final locations may be characterized as displacements in the x and y coordinates of the in-treatment x-ray image between the first set of shift correlation windows and the matching set of shift correlation windows. In operation 228, then, a quality measure may be calculated, for example, as an average displacement in the x and y directions, as illustrated in FIGS. 12A and 12B, for the example of 25 different shift correlation windows. In FIGS. 12A and 12B, the displacements of the shift correlation windows fall within a range with an average value approximately equal to zero. In practice, the choice of the number of shift correlation windows to use, and the displacement of each window, is based on the experience of a clinician and/or clinical data. In other embodiments, different quality measures may be used (e.g., sum of absolute or squared distances).

Figure 13A:
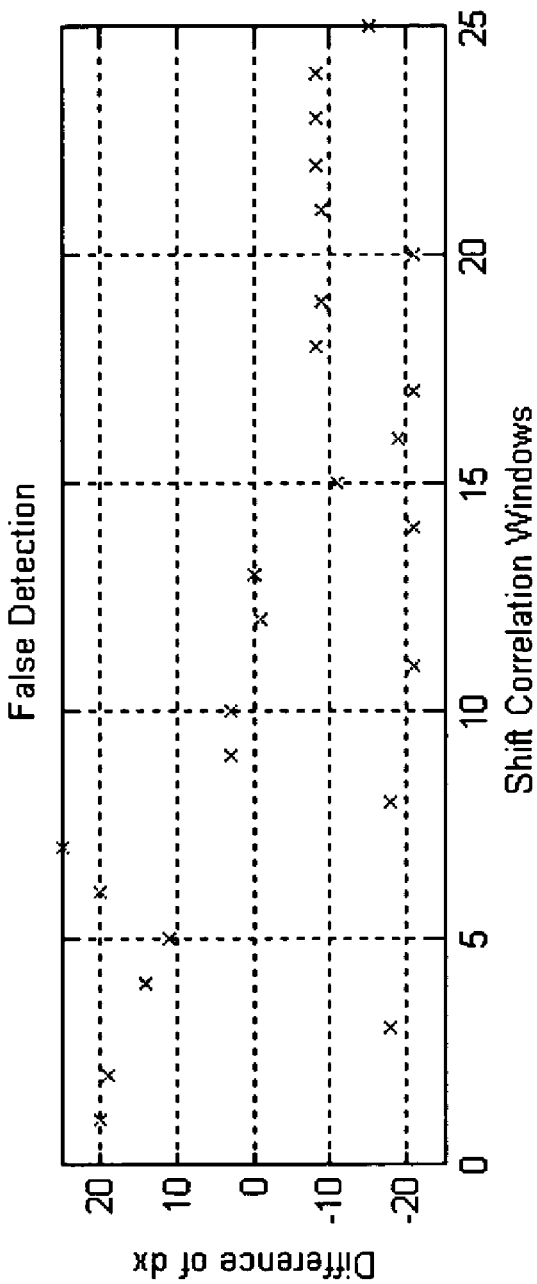
FIGS. 13A and 13B are graphs illustrating a quality measure for incorrect target detection in one embodiment.
Figure 13B:
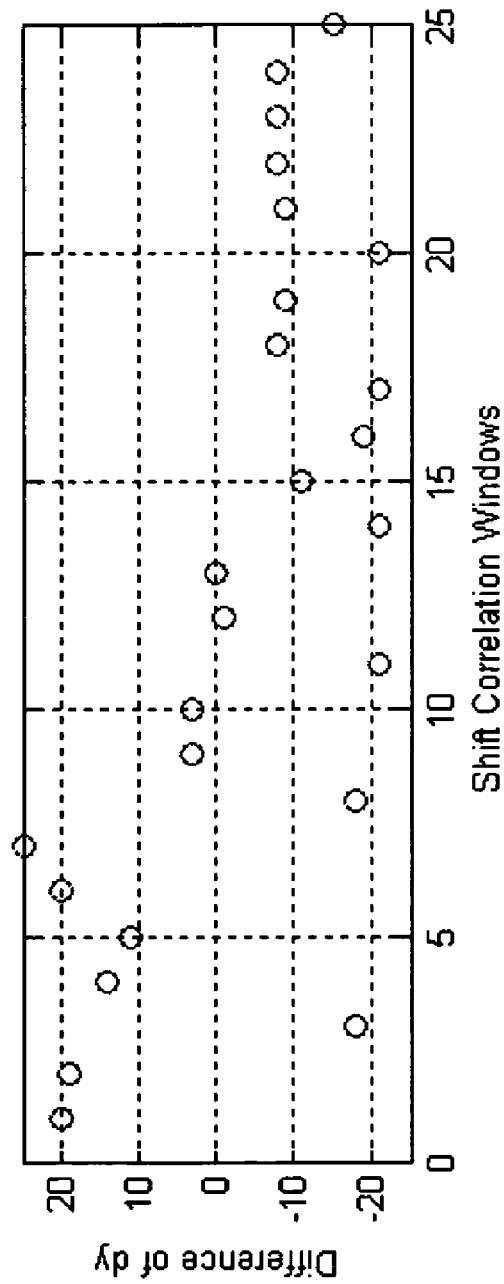
Figures 14A, 14B:
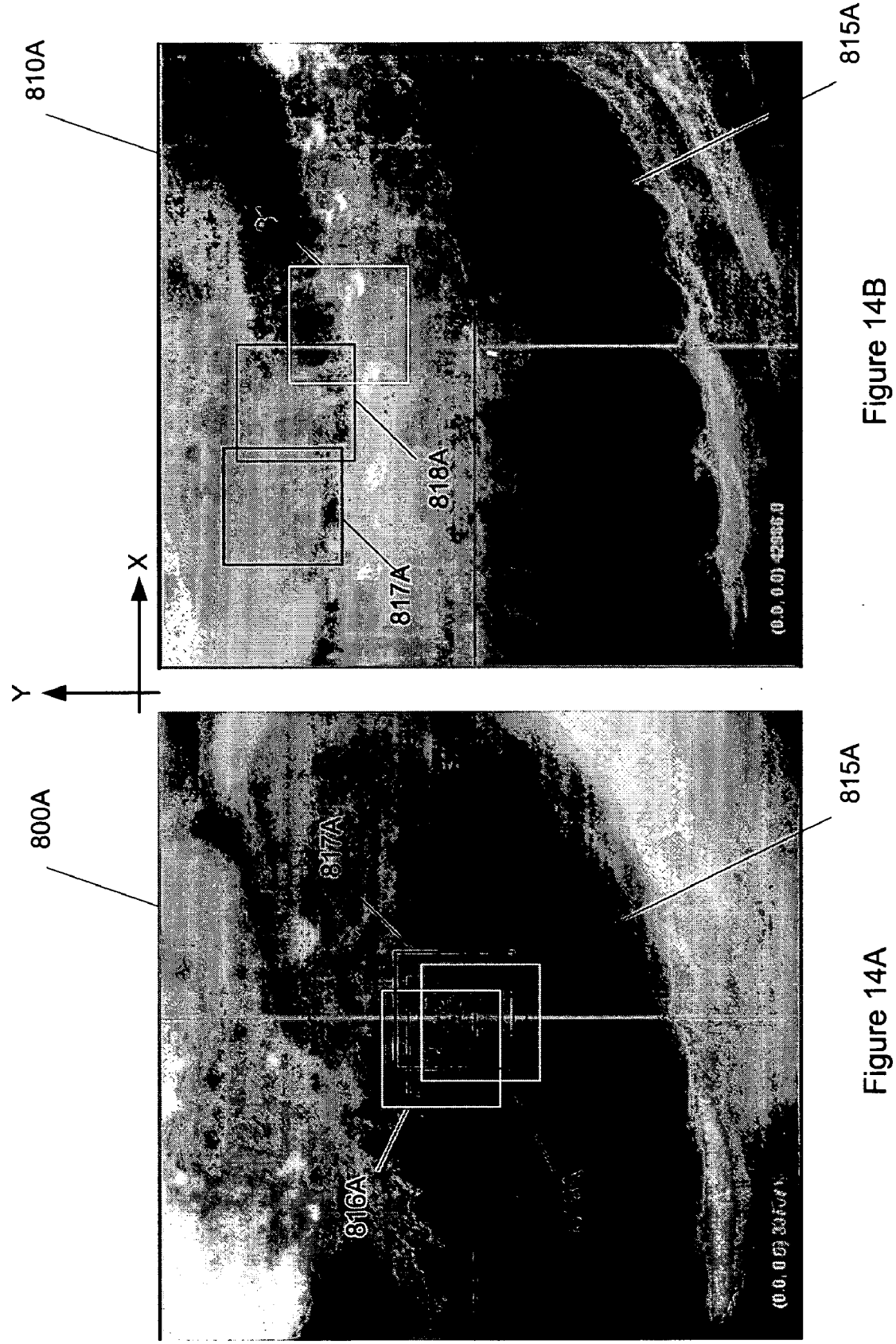
FIGS. 14A and 14B illustrate shift correlation windows corresponding to incorrect target detection in one embodiment.

False or improper tumor detection is illustrated by the graphs of FIGS. 13A and 13B, where the x and y displacements of the shift correlation windows is highly variable and irregular. This result is illustrated in FIGS. 14A and 14B, where the final locations of the shift correlation windows 816A, 817A and 818A are significantly different from their initial location sin DRR 800A and in in-treatment x-ray image 810A.

After the quality measure for the selected ROI in the selected projection has been determined, the process asks, at operation 229 if all ROIs in the selected projected have been tested, and if not, then operations 224-228 are repeated. If all of the ROIs in the selected projection have been tested, then the process asks, at operation 230, if all projections have been tested. If not, then operations 223 through 229 are repeated until all projections have been tested.

Figure 15B:
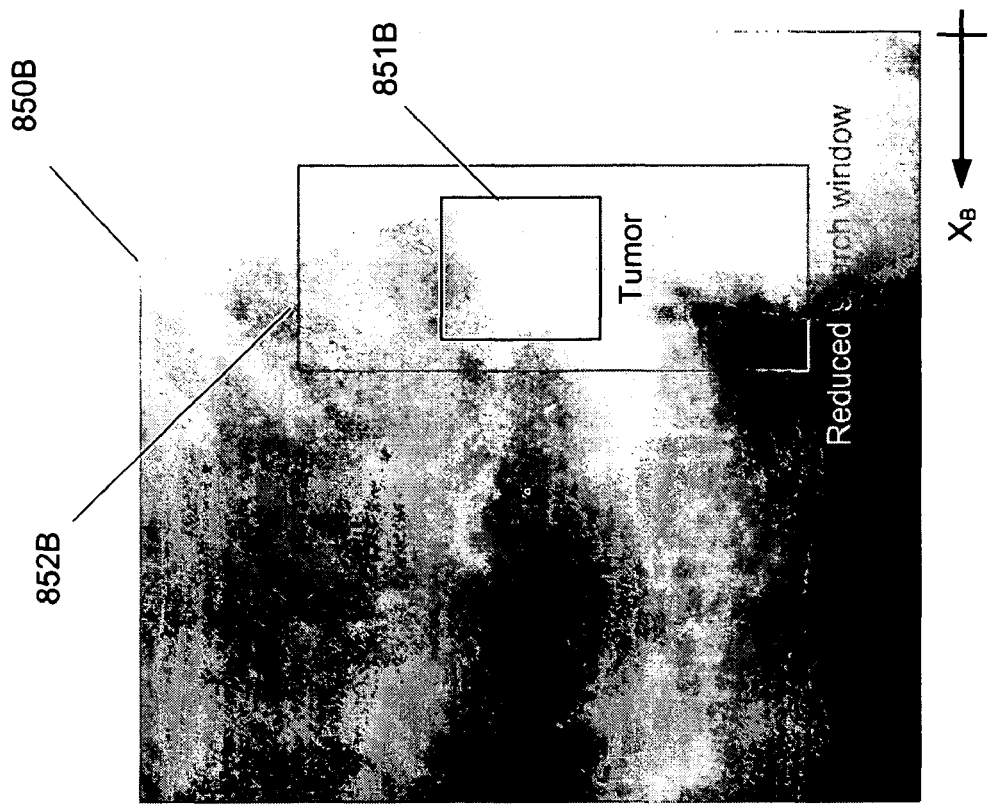
FIGS. 15A and 15B illustrate search window reduction in one embodiment.
Figure 15A:
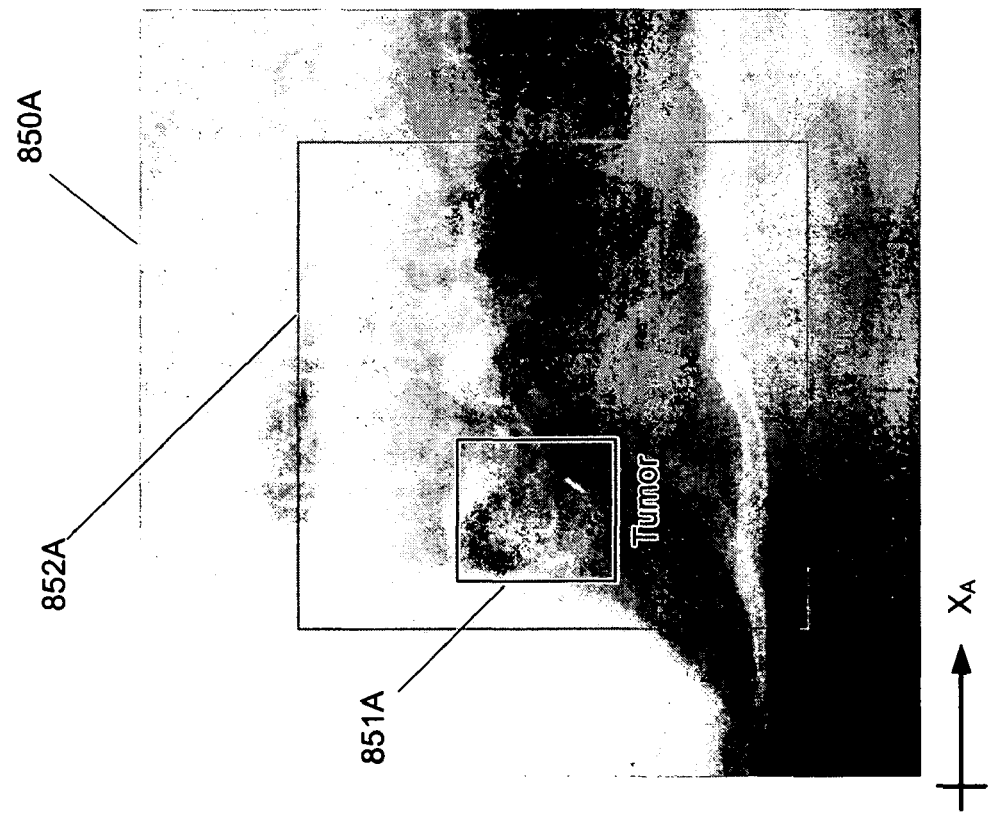

In general, the quality of the in-treatment x-ray images may not be the same in every projection of a volume of interest because the x-rays travel through different paths with different anatomical structures. As a result, the quality of tumor detection in each projection, as determined by the quality measure described above, may be higher in one projection. Thus, operations 227 and 228 may include additional steps. In one embodiment, a high quality target detection in one projection may be used to improve target detection in another projection by constraining a search window in the other projection. FIG. 15A illustrates an in-treatment x-ray image 850A in a first projection of a volume of interest where a tumor 851A has been located within a search window 852A with correct tumor detection as determined by a shift correlation quality measure as described above. As a result, the x and y coordinates of tumor 851A are well-defined. FIG. 15B illustrates an in-treatment x-ray of the volume of interest in a second projection where it is assumed that an initial search has incorrectly detected tumor 851B (the projection of tumor 851A in the second projection) and produced a low quality measure. Because images 850A and 850B share the same x-axis (see FIG. 3A and discussion above), the x-coordinates of tumor 851B are defined by the x-coordinates of tumor 851A and a constrained search window 852B may be defined in image 850B that limits the search in the x-axis and allows the search in the y-axis of image 850B to be optimized.

Figure 16:
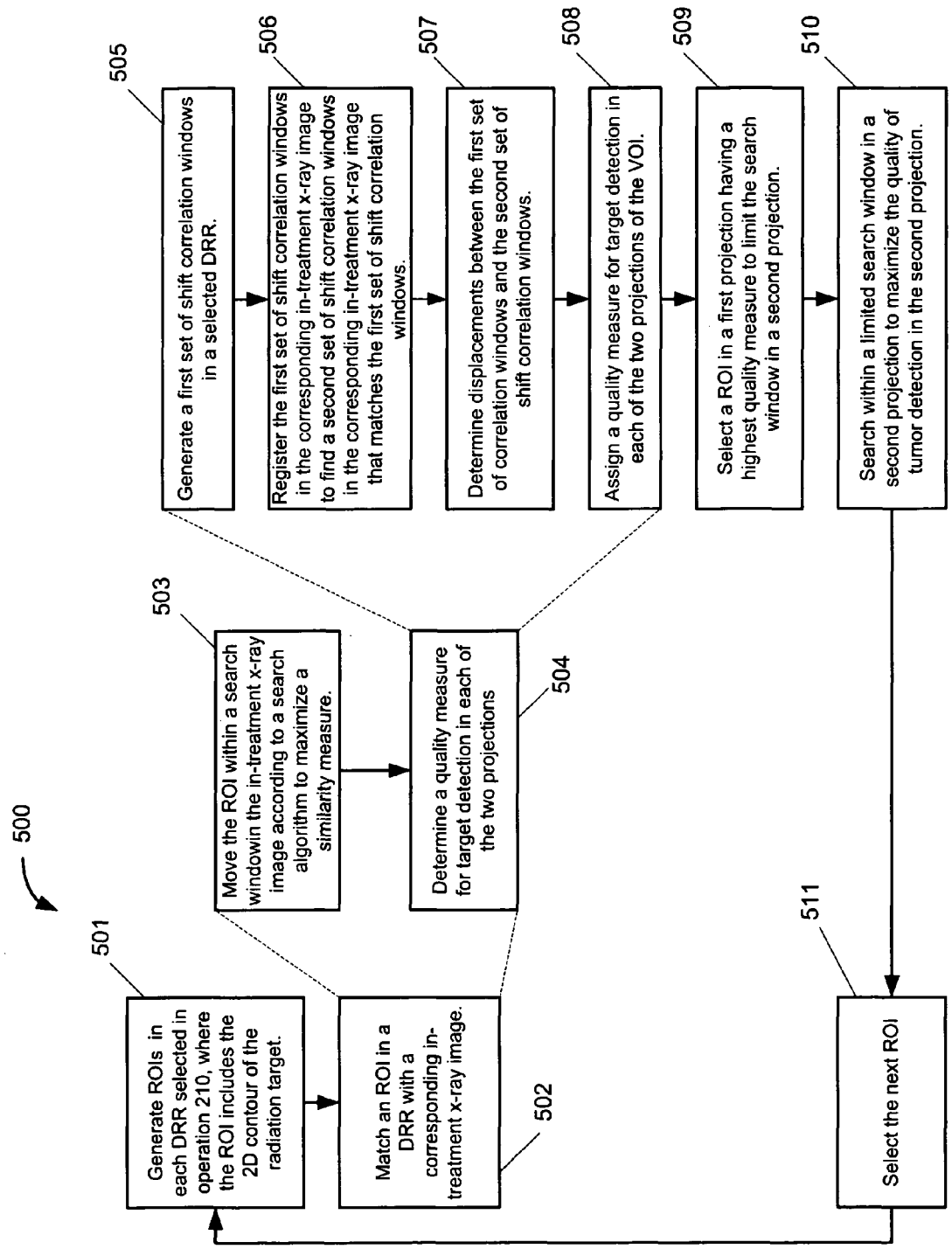
FIG. 16 is a flowchart illustrating a method for target detection in one embodiment.

In certain embodiments, operations in different projections may be performed in parallel. FIG. 16 is a flowchart illustrating one embodiment of a method 500 for target detection. In operation 501, one or more ROIs are generated in the DRRs in the projections corresponding to a patient's global pre-alignment (i.e., operation 210), where each ROI is defined relative to a 2D contour of the radiation target. In operation 502, the ROIs in the DRRs are matched with corresponding in-treatment x-ray images in each projection of the treatment delivery system. Operation 502 includes operations 503 and 504.

In operation 503, the ROI is moved within a search window in the in-treatment x-ray image in each projection according to a search algorithm to maximize a similarity measure. In operation 504, a quality measure for target detection in each projection is determined. Operation 504 includes operations 505 through 509. Operation 505 generates a first set of shift correlation windows in a selected DRR. In operation 506, the first set of shift correlation windows is registered in the corresponding in-treatment x-ray image to find a second set of shift correlation windows in the corresponding in-treatment x-ray image that matches the first set of shift correlation windows, such that the first and second sets of shift correlation windows form matching pairs of shift correlation windows. Operation 507 determines displacements between the matching pairs of shift correlation windows from the first set of shift correlation windows and the second set of shift correlation windows. Operation 508 assigns a quality measure for tumor detection in each projection of the VOI.

The method continues with operation 509, which selects a ROI in a first projection having a highest quality measure in order to limit the search window in a second projection. Next, operation 510 searches within a limited search window in the second projection to maximize the quality of the tumor detection in the second projection. In operation 511, the next ROI in each projection is selected and the method repeats at operation 501.

In one embodiment, a method includes segmenting and removing bony structures from 3D imaging data of a volume of interest (VOI) to visualize a radiation target in DRRs generated from the 3D imaging data; matching the DRRs with in-treatment x-ray images; selecting a region of interest in a DRR including a 2D contour of the radiation target; and searching within a search window in a matching in-treatment x-ray image to match the ROI to a corresponding ROI in the matching in-treatment x-ray image.

Figure 17:
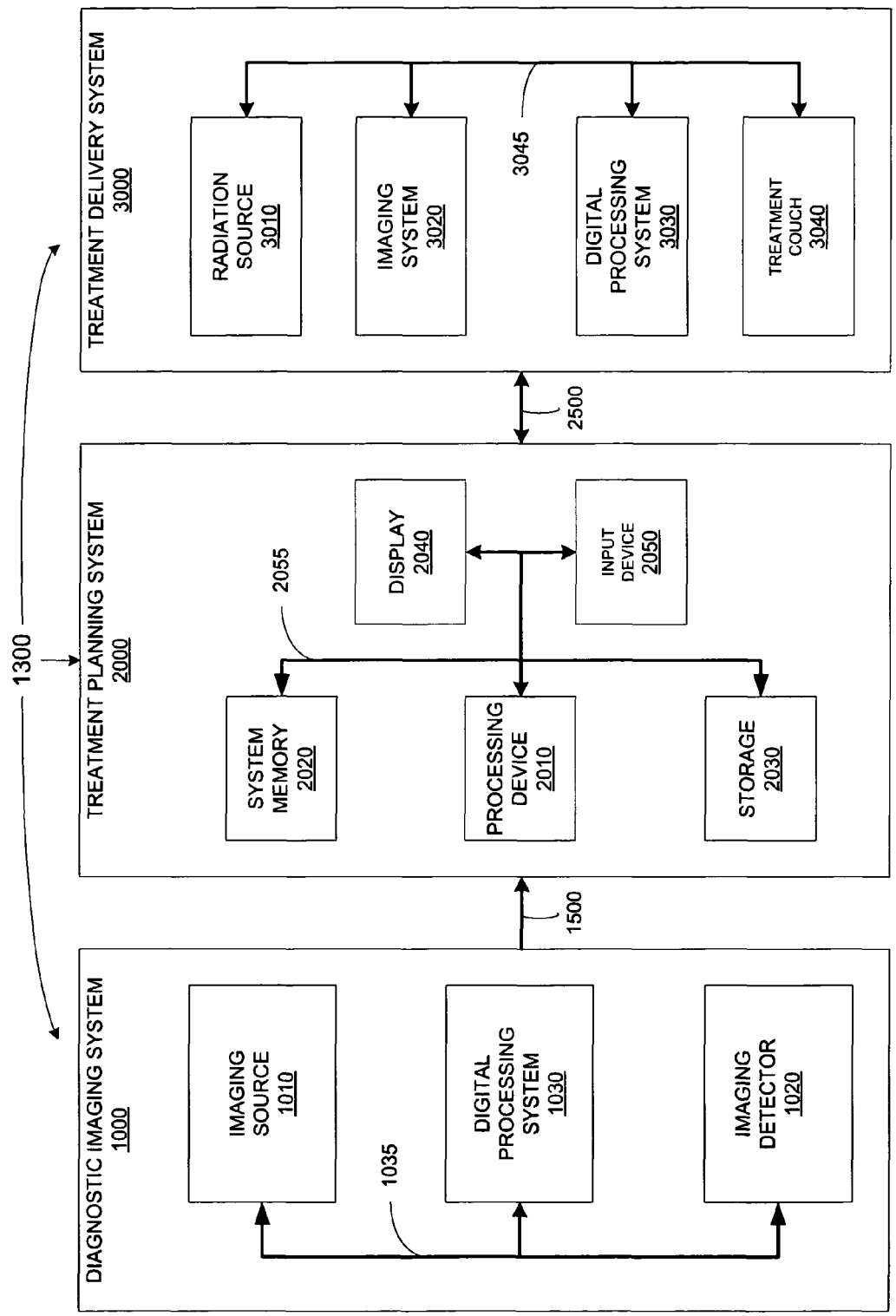
FIG. 17 is a block diagram illustrating a system in which embodiments of the invention may be implemented.

FIG. 17 illustrates one embodiment of systems 1300 that may be used in performing radiation treatment in which embodiments of the present invention may be implemented. As described below and illustrated in FIG. 17, system 1300 may include a diagnostic imaging system 1000, a treatment planning system 2000 and a treatment delivery system 3000.

Diagnostic imaging system 1000 may be any system capable of producing medical diagnostic images of a patient that may be used for subsequent medical diagnosis, treatment planning and/or treatment delivery. For example, diagnostic imaging system 1000 may be a computed tomography (CT) system, a magnetic resonance imaging (MRI) system, a positron emission tomography (PET) system, an ultrasound system or the like. For ease of discussion, diagnostic imaging system 1000 is discussed at times in relation to a CT imaging modality. However, other imaging modalities such as those above may also be used.

Diagnostic imaging system 1000 includes an imaging source 1010 to generate an imaging beam (e.g., x-rays, ultrasonic waves, radio frequency waves, etc.) and an imaging detector 1020 to detect and receive the beam generated by imaging source 1010, or a secondary beam or emission stimulated by the beam from the imaging source (e.g., in an MRI or PET scan). In one embodiment, diagnostic imaging system 1000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used that would be illuminated by each x-ray imaging source. Alternatively, other numbers and configurations of imaging sources and imaging detectors may be used.

The imaging source 1010 and the imaging detector 1020 may be coupled to a digital processing system 1030 to control the imaging operation and process image data. Diagnostic imaging system 1000 includes a bus or other means 1035 for transferring data and commands among digital processing system 1030, imaging source 1010 and imaging detector 1020. Digital processing system 1030 may include one or more general-purpose processors (e.g., a microprocessor), special purpose processor such as a digital signal processor (DSP) or other type of device such as a controller or field programmable gate array (FPGA). Digital processing system 1030 may also include other components (not shown) such as memory, storage devices, network adapters and the like. Digital processing system 1030 may be configured to generate digital diagnostic images in a standard format, such as the DICOM (Digital Imaging and Communications in Medicine) format, for example. In other embodiments, digital processing system 1030 may generate other standard or non-standard digital image formats. Digital processing system 1030 may transmit diagnostic image files (e.g., the aforementioned DICOM formatted files) to treatment planning system 2000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data. Processing device 2010 may represent one or more general-purpose processors (e.g., a microprocessor), special purpose processor such as a digital signal processor (DSP) or other type of device such as a controller or field programmable gate array (FPGA). Processing device 2010 may be configured to execute instructions for performing treatment planning and/or image processing operations discussed herein, such as the spine segmentation tool described herein.

Treatment planning system 2000 may also include system memory 2020 that may include a random access memory (RAM), or other dynamic storage devices, coupled to processing device 2010 by bus 2055, for storing information and instructions to be executed by processing device 2010. System memory 2020 also may be used for storing temporary variables or other intermediate information during execution of instructions by processing device 2010. System memory 2020 may also include a read only memory (ROM) and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning steps discussed herein and/or for storing 3D imaging data and DRRs as discussed herein.

Processing device 2010 may also be coupled to a display device 2040, such as a cathode ray tube (CRT) or liquid crystal display (LCD), for displaying information (e.g., a 2D or 3D representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as treatment delivery system 3000, so that it may not be necessary to export from the treatment planning system prior to treatment delivery. Treatment planning system 2000 may be linked to treatment delivery system 3000 via a data link 2500, which may be a direct link, a LAN link or a WAN link as discussed above with respect to data link 1500. It should be noted that when data links 1500 and 2500 are implemented as LAN or WAN connections, any of diagnostic imaging system 1000, treatment planning system 2000 and/or treatment delivery system 3000 may be in decentralized locations such that the systems may be physically remote from each other. Alternatively, any of diagnostic imaging system 1000, treatment planning system 2000 and/or treatment delivery system 3000 may be integrated with each other in one or more systems.

Treatment delivery system 3000 includes a therapeutic and/or surgical radiation source 3010 to administer a prescribed radiation dose to a target volume in conformance with a treatment plan. Treatment delivery system 3000 may also include an imaging system 3020 to capture intra-treatment images of a patient volume (including the target volume) for registration or correlation with the diagnostic images described above in order to position the patient with respect to the radiation source. Imaging system 3020 may include any of the imaging systems described above. Treatment delivery system 3000 may also include a digital processing system 3030 to control radiation source 3010, imaging system 3020 and a patient support device such as a treatment couch 3040. Digital processing system 3030 may be configured to register 2D radiographic images from imaging system 3020, from two or more stereoscopic projections, with digitally reconstructed radiographs (e.g., DRRs from segmented 3D imaging data) generated by digital processing system 1030 in diagnostic imaging system 1000 and/or DRRs generated by processing device 2010 in treatment planning system 2000. Digital processing system 3030 may include one or more general-purpose processors (e.g., a microprocessor), special purpose processor such as a digital signal processor (DSP) or other type of device such as a controller or field programmable gate array (FPGA). Digital processing system 3030 may also include other components (not shown) such as memory, storage devices, network adapters and the like. Digital processing system 3030 may be coupled to radiation source 3010, imaging system 3020 and treatment couch 3040 by a bus 3045 or other type of control and communication interface.

Digital processing system 3030 may implement methods (e.g., such as method 1200 described above) to register images obtained from imaging system 3020 with pre-operative treatment planning images in order to align the patient on the treatment couch 3040 within the treatment delivery system 3000, and to precisely position the radiation source with respect to the target volume.

The treatment couch 3040 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 3040 may be a component of another mechanical mechanism, such as the Axum® treatment couch developed by Accuray Incorporated of California, or be another type of conventional treatment table known to those of ordinary skill in the art.

Alternatively, treatment delivery system 3000 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target region. In IMRT planning, the optimization algorithm selects subsets of the main beam and determines the amount of time that the patient should be exposed to each subset, so that the prescribed dose constraints are best met. In one particular embodiment, the gantry based system may have a gimbaled radiation source head assembly.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by the treatment planning system, such as the application of a beam (e.g., radiation, acoustic, etc.) and "target" may refer to a non-anatomical object or area.

Embodiments of the present invention include various operations, which are described herein. These operations may be performed by hardware components, software, firmware or a combination thereof. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems such as in a remote diagnosis or monitoring system. In remote diagnosis or monitoring, a user may diagnose or monitor a patient despite the existence of a physical separation between the user and the patient. In addition, the treatment delivery system may be remote from the treatment planning system.

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner. Additionally, some operations may be repeated within an iteration of a particular method.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
   detecting, with a treatment delivery system, a treatment target having motion in up to three translational directions using direct registration of the treatment target, wherein detecting the treatment target comprises:
      generating one or more digitally reconstructed radiographs (DRRs);
      generating a 2D contour of the treatment target on each of the one or more DRRs;
      generating a region of interest (ROI) in each of the one or more DRRs, wherein the ROI includes at least a portion of the 2D contour of the treatment target;
      registering the ROI of each DRR with a corresponding in-treatment image;
      selecting a first in-treatment image that best matches a first ROI in a first corresponding DRR;
      generating a constrained search window in a second in-treatment image; and
      searching within the constrained search window to match the second in-treatment image and a second ROI of a second corresponding DRR;
   tracking the treatment target to synchronize a treatment beam with the motion of the treatment target.

2. The method according to claim 1, wherein registering comprises:
   overlaying each ROI of each DRR on a search window of the corresponding in-treatment image;
   moving each ROI within the search window according to a search algorithm; and
   maximizing a similarity measure between the ROI in each DRR and the search window in the corresponding in-treatment image; and
   wherein selecting the first in-treatment image comprises selecting a best maximized similarity measure from more than one maximized similarity measure, wherein the first in-treatment image has the best maximized similarity measure.

3. The method according to claim 2, wherein registering further comprises:
generating a quality measure for each registration; and
wherein selecting the first in-treatment image further comprises:
selecting a best quality measure, wherein the first in-treatment image has the best quality measure.

4. The method according to claim 3, wherein determining the quality measure comprises:
generating a first plurality of shift correlation windows in each DRR;
registering the first plurality of shift correlation windows in the corresponding in-treatment image to find a second plurality of shift correlation windows in the corresponding in-treatment image that match the first plurality of shift correlation windows, wherein the first plurality of shift correlation windows and the second plurality of shift correlation windows comprise a plurality of shift correlation pairs;
determining a displacement between each shift correlation; and
assigning the quality measure for each registration from the displacement.

5. The method according to claim 2, further comprising computing 3D translations corresponding to locations of the ROIs in the first in-treatment image and the second in-treatment image to determine the location of the target in a 3D treatment frame of reference.

6. The method according to claim 5, further comprising tracking the target with a correlation model between the location of the target and external breathing markers to deliver treatment in synchrony with movement of the target.

7. The method according to claim 5, further comprising:
conforming relative positions of the treatment target and a radiation treatment source to a treatment plan; and
delivering radiation treatment to the treatment target in accordance with the treatment plan.

8. The method according to claim 2, wherein the search algorithm comprises a multi-level search algorithm.

9. The method according to claim 1, further comprising tracking the target with a correlation model between the location of the target and external breathing markers to deliver treatment in synchrony with movement of the target.

10. The method according to claim 1, further comprising pre-aligning a patient in a treatment delivery system, wherein one or more DRRs is matched with a corresponding in-treatment image.

11. The method according to claim 1, further comprising pre-aligning a patient in a treatment coordinate system, wherein pre-aligning the patient comprises matching one or more 2D projections of a segment spine of the patient with 2D in-treatment images of the patient.

12. The method according to claim 1, wherein the one or more DRRs include fiducial markers, and wherein pre-aligning the patient in the treatment coordinate system comprises matching the fiducial markers in the one or more DRRs with 2D in-treatment x-ray images of the patient in one or more corresponding DRRs.

13. The method according to claim 1, wherein the one or more DRRs are derived from 3D imaging data, and wherein the 3D imaging data comprises one or more of computed tomography (CT) image data, magnetic resonance (MR) image data, positron emission tomography (PET) image data and 3D rotational angiography (3DRA) image data for treatment planning.

14. The method according to claim 1, wherein the constrained search window comprises at least one coordinate axis shared between the first in-treatment image and the second in-treatment image.

15. The method of claim 1, further comprising pre-aligning a patient containing the treatment target in a treatment coordinate system of the treatment delivery system, wherein pre-aligning the patient comprises matching one or more digitally reconstructed radiographs (DRRs) with a corresponding x-ray image.

16. The method of claim 1, wherein detecting the treatment target comprises:
generating 2D contours of the treatment target;
generating a region of interest (ROI) in each of one or more digitally reconstructed radiographs (DRRs), wherein the region of interest includes a 2D contour of the treatment target; and
matching the ROI in a DRR with a corresponding x-ray image.

17. The method of claim 1, wherein the treatment target is a lung tumor.

18. A method, comprising:
pre-aligning a patient in a treatment coordinate system, wherein pre-aligning the patient comprises matching two 2D projections of a bony structure of the patient with corresponding 2D in-treatment images of the patient;
detecting, with a treatment delivery system, a treatment target of the patient, the treatment target having motion in up to three translational directions using direct registration of the treatment target; and
tracking the treatment target to synchronize a treatment beam with the motion of the treatment target.

19. The method according to claim 18, wherein the bony structure is the spine.

20. The method according to claim 19, wherein the spine is segmented on the two 2D projections.

21. The method according to claim 18, wherein the two 2D projections are DRRs.

22. A method, comprising:
detecting, with a treatment delivery system, a treatment target having motion in up to three translational directions using direct registration of the treatment target, wherein detecting the treatment target comprises;
selecting region of interest (ROI) in a digitally reconstructed radiograph (DRR) of one or more DRRs in a first projection with a highest quality measure to generate a limited a search window in a second projection;
searching within the limited search window in the second projection to maximize the quality measure in the second projection; and
computing 3D translations corresponding to locations of the ROI in the first projection and the second projection to determine the location of the treatment target in a 3D treatment frame of reference;
tracking the treatment target to synchronize a treatment beam with the motion of the treatment target.

23. The method according to claim 22, further comprising tracking the target with a correlation model between the location of the target and external breathing markers to deliver treatment in synchrony with movement of the target.

24. A method, comprising:
pre-aligning a patient in a treatment coordinate system, wherein pre-aligning the patient comprises matching three or more 2D projections of a segmented spine of the patient with 2D in-treatment x-ray images of the patient in three or more corresponding projections;

detecting, with a treatment delivery system, a patient treatment target having motion in up to three translational directions using direct registration of the treatment target; and tracking the treatment target to synchronize a treatment beam with the motion of the treatment target.

25. An article of manufacture, comprising a non-transitory machine-accessible storage medium including data that, when accessed by a treatment delivery system, cause the treatment delivery system to perform operations comprising:

detecting, by the treatment delivery system, a treatment target having motion in up to three translational directions using direct registration of the treatment target, wherein detecting the treatment target causes the treatment delivery system to perform operations comprising:

generating one or more digitally reconstructed radiographs (DRRs);

generating a 2D contour of the treatment target on each of the one or more DRRs;

generating a region of interest (ROI) in each of the one or more DRRs, wherein the ROI includes at least a portion of the 2D contour of the treatment target;

registering the ROI of each DRR with a corresponding in-treatment image;

selecting a first in-treatment image that best matches a first ROI in a first corresponding DRR;

generating a constrained search window in a second in-treatment image; and searching within the constrained search window to match the second in-treatment image and a second ROI of a second corresponding DRR;

tracking the treatment target to synchronize a treatment beam with the motion of the treatment target.

26. The article of manufacture of claim 25, wherein registering causes the treatment delivery system to perform operations comprising:

overlaying each ROI of each DRR on a search window of the corresponding in-treatment image;

moving each ROI within the search window according to a search algorithm; and maximizing a similarity measure between the ROI in each DRR and the search window in the corresponding in-treatment image; and wherein selecting the first in-treatment image comprises selecting a best maximized similarity measure from more than one maximized similarity measure, wherein the first in-treatment image has the best maximized similarity measure.

27. The article of manufacture of claim 26, wherein registering further causes the treatment delivery system to perform operations comprising:

generating a quality measure for each registration; and
wherein selecting the first in-treatment image further comprises:
selecting a best quality measure, wherein the first in-treatment image has the best quality measure.

28. The article of manufacture of claim 27, wherein determining the quality of the measure causes the treatment delivery system to perform operations comprising:

generating a first plurality of shift correlation windows in each DRR;

registering the first plurality of shift correlation windows in the corresponding in-treatment image to find a second plurality of shift correlation windows in the corresponding in-treatment image that match the first plurality of shift correlation windows, wherein the first plurality of shift correlation windows and the second plurality of shift correlation windows comprise a plurality of shift correlation pairs;

determining a displacement between each shift correlation; and assigning the quality measure for each registration from the displacement.

29. The article of manufacture of claim 26, wherein the machine-accessible storage medium further includes data that cause the non-transitory machine to perform further operations comprising computing 3D translations corresponding to locations of the ROIs in the first in-treatment image and the second in-treatment image to determine the location of the target in a 3D treatment frame of reference.

30. The article of manufacture of claim 29, wherein the machine-accessible storage medium further includes data that cause the non-transitory machine to perform further operations comprising tracking the target with a correlation model between the location of the target and external breathing markers to deliver treatment in synchrony with movement of the target.

31. The article of manufacture of claim 29, wherein the machine-accessible storage medium further includes data that cause the non-transitory machine to perform further operations comprising:

conforming relative positions of the treatment target and a radiation treatment source to a treatment plan; and
delivering radiation treatment to the treatment target in accordance with the treatment plan.

32. The article of manufacture of claim 26, wherein the search algorithm comprises a multi-level search algorithm.

33. The article of manufacture of claim 25, wherein the machine-accessible storage medium further includes data that cause the non-transitory machine to perform further operations comprising tracking the target with a correlation model between the location of the target and external breathing markers to deliver treatment in synchrony with movement of the target.

34. The article of manufacture of claim 25, wherein the machine-accessible storage medium further includes data that cause the non-transitory machine to perform further operations comprising further comprising pre-aligning a patient in a treatment delivery system, wherein one or more DRRs is matched with a corresponding in-treatment image.

35. The article of manufacture of claim 25, wherein the machine-accessible storage medium further includes data that cause the non-transitory machine to perform further operations comprising pre-aligning a patient in a treatment coordinate system, wherein pre-aligning the patient comprises matching one or more 2D projections of a segment spine of the patient with 2D in-treatment images of the patient.

36. The article of manufacture of claim 25, wherein the machine-accessible storage medium further includes data that cause the non-transitory machine to perform further operations comprising:

selecting region of interest (ROI) in a digitally reconstructed radiograph (DRR) of one or more DRRs in a first projection with a highest quality measure to generate a limited a search window in a second projection;

searching within the limited search window in the second projection to maximize the quality measure in the second projection; and computing 3D translations corresponding to locations of the ROI in the first projection and the second projection to determine the location of the target in a 3D treatment frame of reference.

37. The article of manufacture of claim 36, wherein the machine-accessible storage medium further includes data that cause the non-transitory machine to perform further operations comprising tracking the target with a correlation model between the location of the target and external breathing markers to deliver treatment in synchrony with movement of the target.

38. The article of manufacture of claim 25, wherein the one or more DRRs include fiducial markers, and wherein pre-aligning the patient in the treatment coordinate system causes the treatment delivery system to perform operations comprising matching the fiducial markers in the one or more DRRs with 2D in-treatment x-ray images of the patient in one or more corresponding DRRs.

39. The article of manufacture of claim 25, wherein the one or more DRRs are derived from 3D imaging data, and wherein the 3D imaging data comprises one or more of computed tomography (CT) image data, magnetic resonance (MR) image data, positron emission tomography (PET) image data and 3D rotational angiography (3DRA) image data for treatment planning.

40. The article of manufacture of claim 25, wherein the constrained search window comprises at least one coordinate axis shared between the first in-treatment image and the second in-treatment image.

41. A system, comprising:
 a treatment delivery system comprising a first processing device, an imaging system operatively coupled with the first processing device, and a radiation treatment source operatively coupled with the first processing device, wherein the first processing device is configured to control the imaging system to detect a treatment target having motion in up to three translational directions using direct registration of the treatment target, and wherein the first processing device is further configured to control the radiation treatment source to track the treatment target to synchronize a treatment beam of the radiation treatment source with the motion of the treatment target; and
 a treatment planning system including a second processing device and a display device, wherein the second processing device is configured to:
  segment and remove the spine from 3D imaging data of a volume of interest (VOI) to visualize a target, to:
   generate a plurality of digitally reconstructed radiographs (DRRs) from the 3D imaging data in one or more 2D projections of the 3D imaging data, wherein each DRR includes a 2D contour of the target and a region of interest (ROI) around the 2D contour, and to
  display the plurality of DRRs on the display device.

42. A system, comprising:
 a treatment delivery system comprising a first processing device, an imaging system operatively coupled with the first processing device, and a radiation treatment source operatively coupled with the first processing device, wherein the first processing device is configured to control the imaging system to detect a treatment target having motion in up to three translational directions using direct registration of the treatment target, and wherein the first processing device is further configured to control the radiation treatment source to track the treatment target to synchronize a treatment beam of the radiation treatment source with the motion of the treatment target; and
 a treatment planning system comprising a second processing device configured to:
  generate one or more digitally reconstructed radiographs (DRRs);
  generate a 2D contour of the treatment target on each of the one or more DRRs;
  generate a region of interest (ROI) in each of the one or more DRRs,
 wherein the ROI includes at least a portion of the 2D contour of the treatment target; and
 wherein the first processing device is configured to:
  register the ROI of each DRR with a corresponding in-treatment image;
  select a first in-treatment image that best matches a first ROI in a first corresponding DRR;
  generate a constrained search window in a second in-treatment image; and
  search within the constrained search window to match the second in-treatment image and a second ROI of a second corresponding DRR.

* * * * *